(12) United States Patent
Eliasen et al.

(10) Patent No.: US 8,449,606 B2
(45) Date of Patent: May 28, 2013

(54) BALLOON MITRAL SPACER

(75) Inventors: Kenneth Arden Eliasen, Wrentham, MA (US); Steven J. Tallarida, Mansfield, MA (US); Christopher W. Maurer, Wakefield, MA (US); Jonathan E. Wilson, Amesbury, MA (US)

(73) Assignee: Cardiosolutions, Inc., Stoughton, MA (US)

( * ) Notice: Subject to any disclaimer, the term of this patent is extended or adjusted under 35 U.S.C. 154(b) by 288 days.

(21) Appl. No.: 11/748,121

(22) Filed: May 14, 2007

(65) Prior Publication Data

US 2007/0255399 A1    Nov. 1, 2007

Related U.S. Application Data

(63) Continuation-in-part of application No. 11/258,828, filed on Oct. 26, 2005, now Pat. No. 8,092,525.

(51) Int. Cl.
*A61F 2/24*    (2006.01)

(52) U.S. Cl.
USPC ........................................................ 623/2.11

(58) Field of Classification Search
USPC .................. 623/2.11, 2.36, 1.24; 606/195
See application file for complete search history.

(56) References Cited

U.S. PATENT DOCUMENTS

| | | |
|---|---|---|
| 2,549,731 A | 4/1951 | Wattley |
| 2,625,967 A | 1/1953 | Stull |
| 3,197,788 A | 8/1965 | Segger |
| 3,445,916 A | 5/1969 | Schulte |
| 3,551,913 A | 1/1971 | Shiley et al. |
| 3,586,029 A | 6/1971 | Evers et al. |
| 3,589,392 A | 6/1971 | Meyer |
| 3,671,979 A | 6/1972 | Moulopoulos |

(Continued)

FOREIGN PATENT DOCUMENTS

| | | |
|---|---|---|
| EP | 1323438 | 2/2003 |
| EP | 0125393 | 8/2007 |

(Continued)

OTHER PUBLICATIONS

Eisenhauer et al., Closure of Prosthetic Paravalvular Mitral Regurgitation With the Gianturco-Grifka Vascular Occlusion Device, Catheterization and Cardiovascular Interventions, 2001, 5 pages, vol. 54.

(Continued)

*Primary Examiner* — Corrine M McDermott
*Assistant Examiner* — Christina Lauer
(74) *Attorney, Agent, or Firm* — Grossman Tucker Perreault & Pfleger PLLC

(57) ABSTRACT

A heart valve implant according to one embodiment may include a shaft and an anchor disposed on one end of the shaft, the anchor configured to engage tissue. The heart valve implant may further include an expandable member disposed over at least part of the shaft, the expandable member comprising a resiliently deformable internal layer and a resiliently deformable external layer disposed over the internal layer, the expandable member defining a chamber and being configured to receive an inflation medium in the chamber to expand the expandable member, the expandable member further configured to deform upon contact with at least a portion of at least one leaflet of a heart valve to at least partially conform to the shape of the leaflet.

11 Claims, 19 Drawing Sheets

U.S. PATENT DOCUMENTS

| | | | |
|---|---|---|---|
| 3,689,942 A | 9/1972 | Rapp | |
| 3,714,671 A | 2/1973 | Edwards et al. | |
| 3,739,402 A | 6/1973 | Cooley et al. | |
| 3,983,581 A | 10/1976 | Angell et al. | |
| 4,079,468 A | 3/1978 | Liotta et al. | |
| 4,084,268 A | 4/1978 | Ionescu et al. | |
| 4,259,753 A | 4/1981 | Liotta et al. | |
| 4,291,420 A | 9/1981 | Reul | |
| 4,297,749 A | 11/1981 | Davis et al. | |
| 4,439,185 A * | 3/1984 | Lundquist | 604/97.02 |
| 4,535,757 A | 8/1985 | Webster, Jr. | |
| 4,597,767 A | 7/1986 | Lenkei | |
| 4,865,030 A | 9/1989 | Polyak | |
| 4,960,424 A | 10/1990 | Grooters | |
| 5,217,484 A | 6/1993 | Marks | |
| 5,222,973 A | 6/1993 | Sharpe et al. | |
| 5,261,916 A | 11/1993 | Engelson | |
| 5,304,195 A | 4/1994 | Twyford, Jr. et al. | |
| 5,308,357 A | 5/1994 | Lichtman | |
| 5,318,589 A | 6/1994 | Lichtman | |
| 5,350,397 A | 9/1994 | Palermo et al. | |
| 5,397,351 A | 3/1995 | Pavcnik et al. | |
| 5,411,552 A | 5/1995 | Andersen et al. | |
| 5,415,667 A | 5/1995 | Frater | |
| 5,462,527 A | 10/1995 | Stevens-Wright et al. | |
| 5,509,428 A | 4/1996 | Dunlop | |
| 5,582,607 A | 12/1996 | Lackman | |
| 5,611,800 A | 3/1997 | Davis et al. | |
| 5,634,936 A * | 6/1997 | Linden et al. | 606/213 |
| 5,638,827 A | 6/1997 | Palmer et al. | |
| 5,649,949 A | 7/1997 | Wallace et al. | |
| 5,653,712 A | 8/1997 | Stern | |
| 5,665,100 A | 9/1997 | Yoon | |
| 5,776,075 A | 7/1998 | Palmer | |
| 5,792,179 A | 8/1998 | Sideris | |
| 5,797,958 A | 8/1998 | Yoon | |
| 5,814,098 A | 9/1998 | Hinnenkamp et al. | |
| 5,840,081 A | 11/1998 | Andersen et al. | |
| 5,891,130 A | 4/1999 | Palermo et al. | |
| 5,895,391 A | 4/1999 | Farnholtz | |
| 5,928,224 A | 7/1999 | Laufer | |
| 5,957,865 A | 9/1999 | Backman et al. | |
| 5,957,949 A | 9/1999 | Leonhardt et al. | |
| 5,989,242 A | 11/1999 | Saadat et al. | |
| 5,993,474 A | 11/1999 | Ouchi | |
| 6,090,096 A | 7/2000 | St. Goar et al. | |
| 6,152,144 A | 11/2000 | Lesh et al. | |
| 6,168,614 B1 | 1/2001 | Andersen et al. | |
| 6,190,373 B1 | 2/2001 | Palermo et al. | |
| 6,217,610 B1 | 4/2001 | Carpentier et al. | |
| 6,283,127 B1 | 9/2001 | Sterman et al. | |
| 6,283,995 B1 | 9/2001 | Moe et al. | |
| 6,287,339 B1 | 9/2001 | Vazquez et al. | |
| 6,332,893 B1 | 12/2001 | Mortier et al. | |
| 6,358,277 B1 | 3/2002 | Duran | |
| 6,415,693 B1 | 7/2002 | Simon et al. | |
| 6,419,695 B1 | 7/2002 | Gabbay | |
| 6,440,132 B1 | 8/2002 | Jackson | |
| 6,454,798 B1 | 9/2002 | Moe | |
| 6,461,382 B1 | 10/2002 | Cao | |
| 6,482,228 B1 | 11/2002 | Norred | |
| 6,508,825 B1 | 1/2003 | Selmon et al. | |
| 6,592,606 B2 | 7/2003 | Huter et al. | |
| 6,652,578 B2 * | 11/2003 | Bailey et al. | 623/1.24 |
| 6,673,100 B2 | 1/2004 | Diaz et al. | |
| 6,682,559 B2 | 1/2004 | Myers et al. | |
| 6,695,866 B1 | 2/2004 | Kuehn et al. | |
| 6,746,404 B2 | 6/2004 | Schwartz | |
| 6,764,510 B2 | 7/2004 | Vidlund et al. | |
| 6,767,362 B2 | 7/2004 | Schreck | |
| 6,769,434 B2 | 8/2004 | Liddicoat et al. | |
| 6,805,711 B2 | 10/2004 | Quijano et al. | |
| 6,821,297 B2 | 11/2004 | Snyders | |
| 6,830,584 B1 | 12/2004 | Seguin | |
| 6,830,585 B1 | 12/2004 | Artof et al. | |
| 6,849,081 B2 | 2/2005 | Sepetka et al. | |
| 6,869,444 B2 | 3/2005 | Gabbay | |
| 6,896,700 B2 | 5/2005 | Lu et al. | |
| 6,911,043 B2 | 6/2005 | Myers et al. | |
| 6,971,998 B2 | 12/2005 | Rosenman et al. | |
| 6,974,476 B2 | 12/2005 | McGuckin, Jr. et al. | |
| 7,018,406 B2 | 3/2006 | Seguin et al. | |
| 7,056,286 B2 | 6/2006 | Ravenscroft et al. | |
| 7,070,618 B2 | 7/2006 | Streeter | |
| 7,077,862 B2 | 7/2006 | Vidlund et al. | |
| 7,101,395 B2 | 9/2006 | Tremulis et al. | |
| 7,112,219 B2 | 9/2006 | Vidlund et al. | |
| 7,160,322 B2 | 1/2007 | Gabbay | |
| 7,189,199 B2 | 3/2007 | McCarthy et al. | |
| 7,247,134 B2 | 7/2007 | Vidlund et al. | |
| 7,344,553 B2 | 3/2008 | Opolski et al. | |
| 7,374,572 B2 | 5/2008 | Gabbay | |
| 7,381,210 B2 | 6/2008 | Zarbatany et al. | |
| 7,404,824 B1 * | 7/2008 | Webler et al. | 623/2.36 |
| 7,678,145 B2 | 3/2010 | Vidlund et al. | |
| 7,753,949 B2 | 7/2010 | Lamphere et al. | |
| 7,785,366 B2 | 8/2010 | Maurer et al. | |
| 8,092,525 B2 | 1/2012 | Eliasen et al. | |
| 8,216,302 B2 | 7/2012 | Wilson et al. | |
| 2001/0007956 A1 | 7/2001 | Letac et al. | |
| 2001/0010017 A1 | 7/2001 | Cribier et al. | |
| 2002/0042651 A1 | 4/2002 | Liddicoat et al. | |
| 2002/0058995 A1 | 5/2002 | Stevens | |
| 2002/0077566 A1 * | 6/2002 | Laroya et al. | 600/585 |
| 2002/0081553 A1 | 6/2002 | Tramonte | |
| 2002/0183838 A1 | 12/2002 | Liddicoat et al. | |
| 2002/0188170 A1 | 12/2002 | Santamore et al. | |
| 2003/0033009 A1 | 2/2003 | Gabbay | |
| 2003/0040792 A1 | 2/2003 | Gabbay | |
| 2003/0105519 A1 | 6/2003 | Fasol et al. | |
| 2003/0130731 A1 | 7/2003 | Vidlund et al. | |
| 2003/0139751 A1 | 7/2003 | Evans et al. | |
| 2003/0144574 A1 | 7/2003 | Heilman et al. | |
| 2003/0181945 A1 | 9/2003 | Opolski et al. | |
| 2003/0199975 A1 | 10/2003 | Gabbay | |
| 2003/0208203 A1 | 11/2003 | Lim et al. | |
| 2003/0212453 A1 | 11/2003 | Mathis et al. | |
| 2004/0034366 A1 | 2/2004 | van der Burg et al. | |
| 2004/0044402 A1 | 3/2004 | Jung et al. | |
| 2004/0088047 A1 | 5/2004 | Spence et al. | |
| 2004/0106989 A1 | 6/2004 | Wilson et al. | |
| 2004/0122512 A1 | 6/2004 | Navia et al. | |
| 2004/0127981 A1 | 7/2004 | Rahdert et al. | |
| 2004/0127983 A1 | 7/2004 | Mortier et al. | |
| 2004/0148020 A1 | 7/2004 | Vidlund et al. | |
| 2004/0181256 A1 | 9/2004 | Glaser | |
| 2004/0210304 A1 | 10/2004 | Seguin et al. | |
| 2004/0210307 A1 | 10/2004 | Khairkhahan | |
| 2004/0225353 A1 | 11/2004 | McGuckin, Jr. et al. | |
| 2004/0225354 A1 | 11/2004 | Allen et al. | |
| 2004/0243229 A1 | 12/2004 | Vidlund et al. | |
| 2005/0021056 A1 | 1/2005 | Goar et al. | |
| 2005/0033446 A1 | 2/2005 | Deem et al. | |
| 2005/0038508 A1 | 2/2005 | Gabbay | |
| 2005/0038509 A1 | 2/2005 | Ashe | |
| 2005/0065591 A1 | 3/2005 | Moberg et al. | |
| 2005/0070999 A1 | 3/2005 | Spence | |
| 2005/0075727 A1 | 4/2005 | Wheatley | |
| 2005/0090824 A1 | 4/2005 | Shluzas et al. | |
| 2005/0131451 A1 | 6/2005 | Kleshinski et al. | |
| 2005/0159810 A1 | 7/2005 | Filsoufi | |
| 2005/0222488 A1 | 10/2005 | Chang et al. | |
| 2005/0288786 A1 | 12/2005 | Chanduszko | |
| 2006/0025855 A1 * | 2/2006 | Lashinski et al. | 623/2.1 |
| 2006/0058871 A1 | 3/2006 | Zakay et al. | |
| 2006/0084943 A1 | 4/2006 | Rosenman et al. | |
| 2006/0129025 A1 | 6/2006 | Levine et al. | |
| 2006/0149368 A1 | 7/2006 | Spence | |
| 2006/0155326 A1 | 7/2006 | Aranyi | |
| 2006/0178700 A1 | 8/2006 | Quinn | |
| 2006/0195012 A1 | 8/2006 | Mortier et al. | |
| 2006/0195185 A1 | 8/2006 | Lane et al. | |
| 2006/0199995 A1 | 9/2006 | Vijay | |
| 2006/0229708 A1 | 10/2006 | Powell et al. | |
| 2006/0241745 A1 | 10/2006 | Solem | |
| 2006/0253072 A1 | 11/2006 | Pai et al. | |
| 2006/0293698 A1 | 12/2006 | Douk | |

| | | | |
|---|---|---|---|
| 2007/0049980 | A1 | 3/2007 | Zielinski et al. |
| 2007/0093890 | A1 | 4/2007 | Eliasen et al. |
| 2007/0118151 | A1 | 5/2007 | Davidson |
| 2007/0167981 | A1 | 7/2007 | Opolski et al. |
| 2007/0185571 | A1 | 8/2007 | Kapadia et al. |
| 2007/0198050 | A1 | 8/2007 | Ravenscroft et al. |
| 2007/0198082 | A1 | 8/2007 | Kapadia et al. |
| 2007/0213578 | A1 | 9/2007 | Khairkhahan et al. |
| 2007/0232981 | A1 | 10/2007 | Ravenscroft et al. |
| 2007/0239154 | A1 | 10/2007 | Shaolian et al. |
| 2007/0265700 | A1 | 11/2007 | Eliasen et al. |
| 2007/0282429 | A1 | 12/2007 | Hauser et al. |
| 2007/0293943 | A1 | 12/2007 | Quinn |
| 2008/0125860 | A1 | 5/2008 | Webler et al. |
| 2008/0125861 | A1 | 5/2008 | Webler et al. |
| 2008/0183105 | A1 | 7/2008 | Greenhalgh et al. |
| 2008/0195200 | A1 | 8/2008 | Vidlund et al. |
| 2008/0288061 | A1 | 11/2008 | Maurer et al. |
| 2009/0043382 | A1 | 2/2009 | Maurer et al. |
| 2009/0048668 | A1 | 2/2009 | Wilson et al. |
| 2009/0105814 | A1 | 4/2009 | Groothuis et al. |
| 2009/0131849 | A1 | 5/2009 | Maurer et al. |
| 2009/0131880 | A1 | 5/2009 | Speziali et al. |
| 2009/0132033 | A1 | 5/2009 | Maurer et al. |
| 2009/0163934 | A1 | 6/2009 | Raschdorf, Jr. et al. |
| 2009/0240326 | A1 | 9/2009 | Wilson et al. |
| 2010/0022948 | A1 | 1/2010 | Wilson et al. |
| 2010/0324668 | A1 | 12/2010 | Maurer et al. |
| 2012/0143320 | A1 | 6/2012 | Eliasen et al. |

FOREIGN PATENT DOCUMENTS

| | | |
|---|---|---|
| GB | 1264472 | 2/1972 |
| GB | 1268484 | 3/1972 |
| GB | 1388064 | 3/1975 |
| WO | 03/049619 | 6/2003 |
| WO | 2006032051 | 3/2006 |
| WO | 2006/064490 A1 | 6/2006 |
| WO | 2006091597 | 8/2006 |
| WO | 2006/111391 | 10/2006 |
| WO | 2006127509 | 11/2006 |
| WO | 2007064810 | 6/2007 |
| WO | 2007078772 | 7/2007 |
| WO | 2007100409 | 9/2007 |
| WO | 2007/140470 A2 | 12/2007 |
| WO | 2008079828 | 7/2008 |
| WO | 2009053952 A2 | 4/2009 |

OTHER PUBLICATIONS

Hourihan et al., Transcatheter Umbrella Closure of Valvular and Paravalvular Leaks, American College of Cardiology, Nov. 15, 1992, 7 pages, vol. 20, No. 6.

Moscucci et al., Coil Embolization of a Periprosthetic Mitral Valve Leak Associated With Severe Hemolytic Anemia, Images in Cardiovascular Medicine, American Heart Association, Inc., 2001, 2 pages, vol. 104.

Rashkind et al. Nonsurgical closure of patent ductus arteriosus: clinical application of the Rashkind PDA Occluder System, Therapy and Prevention—Congenital Heart Disease, Mar. 1987, 10 pages, vol. 75, No. 3.

Ryhänen et al., Invivo biocompatibility evaluation of nickel-titanium shape memory metal alloy: Muscle and perineural tissue responses and encapsule membrane thickness, Muscle and Perineural Tissue Response to Nitinol, accepted Jan. 19, 1998, 8 pages.

International Search Report and Written Opinion dated Jan. 16, 2009 issued in PCT Application No. PCT/US08/83497, 10 pages.

Criber et al., Treatment of Calcific Aortic Stenosis With the Percutaneous Health Valve—Mid-Term Follow-Up From the Initial Feasibility Studies: The French Experience, Journal of the American College of Cardiology, Mar. 21, 2006, vol. 47, No. 6, 1241-1223.

Douthitt, Cardiac Dimensions® Inc. Receives CE Mark for CARILLON™ Mitral Contour System™, Cardiac Dimensions—News, htpp://www.cardiacdimensions.com/usa/press-release-2-4-09.html, downloaded Feb. 24, 2009, 1-2.

Eltchaninoff, Clinical results of percutaneous aortic valve implantation, Euro PCR07, Cribier-Edwards, 30 pages.

Fitts et al., Fluoroscopy-Guided Femoral Artery Puncture Reduces the Risk of PCI-Related Vascular Complications, Journal of Interventional Cardiology, vol. 21, No. 3, 2008, 273-278.

Gelsomino et al., Left ventricular diastolic function after restrictive mitral ring annuloplasty in chronic ischemic mitral regurgitation and its predictive value on outcome and recurrence of regurgitation, International Journal of Cardiology, vol. 132, 2009, 419-428.

Hytowitz, First U.S. Patients Enrolled in the Realism Continued Access Study, evalve, http://www.evalveinc.com/europe/press/22/html, downloaded Feb. 24, 2009, 2 pages.

International Search Report and Written Opinion dated Feb. 25, 2009 issued in PCT Application No. PCT/US08/83570, 13 pages.

Onundarson et al., Warfarin anticoagulation intensity in specialist-based and in computer-assisted dosing practice, International Journal of Laboratory Hematology, 2008, vol. 30, 382-389.

Fukuda et al., Maintenance of Geometric Alterations Associated with Percutaneous Mitral Valve Repair: Real-Time Three-Dimensional Echocardiographic Assessment in an Ovine Model, J. Heart Valve Dis, May 2008, vol. 17, No. 3, 276-282.

Vahanian, The Cardiologist's Perspective on the Future of Percutaneous Mitral Valve Repair, Euro PCR07, 53 pages.

Vahanian, Edwards MONARC system—Evolution Interim Results, 31 pages.

Vranckx et al., The TandemHeart©, percutaneous transseptal left ventricular assist device: a safeguard in high-risk percutaneous coronary interventions. The six-year Rotterdam experience, Clinical research EuroInterv., 2008, vol. 4, 331-337.

Wolf et al., Solid and gaseous cerebral microembolization after biologic and mechanical aortic valve replacement: Investigation with multirange and multifrequency transcranial Doppler ultrasound, The Journal of Thoracic and Cardiovascular Surgery, Mar. 2008, vol. 135, No. 3, 512-520.

Xiangming et al., In Vivo Characterization of Attachment Safety Between Cardiac Pacing Lead and Canine Heart Muscle*, Acta Mechanica Solida Sinica, Sep. 2007, vol. 20, No. 3, 189-197.

Matthews, Anatomy of the Heart, Definitions Cardiology Explained and Presented by Robert Matthews, MD, http://www.rjmatthewsmd.com/Definitions/anatomy_ofthe_heart.htm, printed Jul. 28, 2008, 265 pages.

Mullens, Vascular access, Cardiac Catheterization in Congenital Heart Disease; Pediatric and Adult, 2006, Chapter 4, pp. 115-117, 5 pages, Blackwell Futura, USA.

Mullens, Aortic valve dilation, Cardiac Catheterization in Congenital Heart Disease; Pediatric and Adult, 2006, Chapter 19, pp. 487-489, 5 pages, Blackwell Futura, USA.

Mullens, Foreign body removal, Cardiac Catheterization in Congenital Heart Disease; Pediatric and Adult, 2006, Chapter 12, pp. 350-377, 30 pages, Blackwell Futura, USA.

Mullens, Flow directed catheters ("floating" balloon catheters), Cardiac Catheterization in Congenital Heart Disease; Pediatric and Adult, 2006, Chapter 7, pp. 213-221, 9 pages, Blackwell Futura, USA.

International Search Report and Written Opinion, May 11, 2007 (6 pages).

Trippel, et al., "Reinforced Ivalon Sponge as an Aortic Prosthesis" Feb. 1960 (9 pages).

Johns, et al., "Mitral Insufficiency: the Experimental Use of a Mobile Polyvinyl Sponge Prosthesis" Sep. 1954 (pp. 335-341).

Glenn, et al., "The Surgical Treatment of Mitral Insufficiency: the Fate of a Vascularized Transchamber Intracardiac Graft" Apr. 1955 (pp. 510-518).

Carter, et al. "Surgical Treatment of Mitral Insufficiency" 1953 (pp. 574-583).

Harken, et al., "The Surgical Treatment of Mitral Insufficiency" 1954 (pp. 604-627).

Benichoux, et al., "A Method of Surgical Correction of Mitral Insufficiency" 1955 (pp. 148-158).

Glenn, et al., "The Surgical Treatment of Mitral Insufficiency with Particular Reference to the Application of a Vertically Suspended Graft" Jul. 1956 (pp. 59-77).

Harken, et al., "The Surgical Correction of Mitral Insufficiency" 1953 (pp. 4-7).

Sakakibara, "A Surgical Approach to the Correction of Mitral Insufficiency" Aug. 1955 (pp. 196-203).
Bailey, et al., "Surgical Repair of Mitral Insufficiency" Feb. 1951 (pp. 125-182).
Bailey, et al., "Closed Intracardiac Tactile Surgery" Jul. 1952 (pp. 1-24).
Blalock, "A Consideration of Some of the Problems in Cardiovascular Surgery" Jun. 1951 (pp. 543-571).
Bailey, et al., "The Surgical Correction of Mitral Insufficiency by the Use of Pericardial Grafts" Dec. 1954 (pp. 551-627).
Borrie, "Mitral Insufficiency: Experimental Circular Suture Around the Atrioventricular Ring" 1955 (pp. 687-697).
Moore, et al., "Unsuitability of Transventricular Autogenous Slings for Diminishing Valvular Insufficiency" Feb. 1953 (pp. 173-182).
Henderson, et al., "The Surgical Treatment of Mitral Insufficiency" Jun. 1953 (pp. 858-868).
Glover, et al., "The Fate of Intracardiac Pericardial Grafts as Applied to the Closure of Septal Defects and to the Relief of Mitral Insufficiency" 1952 (pp. 178-185).
Glenn, et al., "The Implantation of a Vascularized Graft in the Chambers of the Heart" 1954 (pp. 5-11).
Acar et al., AREVA: Multicenter Randomized Comparison of Low-Dose Versus Standard-Dose Anticoagulation in Patients With Mechanical Prosthetic Heart Valves, Circulation, Nov. 1, 1996, 2107-12, vol. 94, No. 9.
Acker et al., Mitral valve surgery in heart failure: Insights from the Acorn Clinical Trial, Surgery for Acquired Cardiovascular Disease, The Journal of Thoracic and Cardiovascular Surgery, Sep. 2006, 568-577.e4, vol. 132, No. 3.
Babaliaros et al., Emerging Applications for Transseptal Left Heart Catheterization—Old Techniques for New Procedures, Journal of the American College of Cardiology, Jun. 3, 2008, 2116-22, vol. 51, No. 22.
Kuck et al., Best of Structural Heart Disease Abstracts, TCT-124, The American Journal of Cardiology, Oct. 20-25, 2007, 58L.
Rinaldi et al., Best of Structural Heart Disease Abstracts, TCT-123, The American Journal of Cardiology, Oct. 20-25, 2007, 57L.
Siminiak et al., Best of Structural Heart Disease Abstracts, TCT-125, The American Journal of Cardiology, Oct. 20-25, 2007, 58L.
B-Lundqvist et al., Transseptal Left Heart Catheterization: A Review of 278 Studies, Clin. Cardiol., Jan. 1986, 21-26, vol. 9.
Bonow et al., ACC/AHA 2006 Guidelines for the Management of Patients With Valvular Heart Disease: Executive Summary, Circulation—Journal of the American Heart Association, Downloaded from circ.ahajournals.org, Jul. 31, 2008, 449-527.
Braunberger et al., Very Long-Term Results (More Than 20 Years) of Valve Repair With Carpentier's Techniques in Nonrheumatic Mitral Valve Insufficiency, Downloaded from circ.ahajournals.org, Aug. 26, 2008, I-8-I-11.
Bryan et al., Prospective randomized comparison of CarboMedics and St. Jude Medical bileaflet mechanical heart valve prostheses: Ten-year follow-up, The Journal of Thoracic and Cardiovascular Surgery, Mar. 2007, 614-622.e2, vol. 133, No. 3.
Burkhoff et al., A randomized multicenter clinical study to evaluate the safety and efficacy of the TandemHeart percutaneous ventricular assist device versus conventional therapy with intraaortic balloon pumping for treatment of cardiogenic shock, American Heart Journal, Sep. 2006, 469.e1-469.e8, vol. 152, No. 3.
Byrne et al., Percutaneous Mitral Annular Reduction Provides Continued Benefit in an Ovine Model of Dilated Cardiomyopathy, Downloaded from circ.ahajournals.org, Aug. 26, 2008, 3088-92.
Carpentier et al., Reconstructive surgery of mitral valve incompetence Ten-year appraisal, The Journal of Thoracic and Cardiovascular Surgery, Mar. 1980, 338-348, vol. 79, No. 3.
Casselman et al., Mitral Valve Surgery Can Now Routinely Be Performed Endoscopically, Downloaded from circ.ahajournals.org, Aug. 26, 2008, II-48-II-54.
Cauchemez et al., High-Flow Perfusion of Sheaths for Prevention of Thromboembolic Complications During Complex Catheter Ablation in the Left Atrium, Journal of Cardiovascular Electrophysiology, Mar. 2004, 276-283, vol. 15, No. 3.
ClinicalTrials.gov, Aachen Safety and Efficacy of the Percutaneous Transvenous Mitral Annuloplasty Device to Reduce Mitral Regurgitation (PTOLEMY), http://clinicaltrials.gov/ct2/show/NCT00572091?term=mitral+regurgitation&rank=2, Aug. 25, 2008, 1-3.
ClinicalTrials.gov, Feasibility Study of a Percutaneous Mitral Valve Repair System., http://clinicaltrials.gov/ct2/show/NCT00209339?term=mitral+valve&rank=3, Aug. 25, 2008, 1-4.
ClinicalTrials.gov, Montreal Safety and Efficacy of the Percutaneous Transvenous Mitral Annuloplasty Device (PTOLEMY), http://clinicaltrials.gov/ct2/show/NCT00571610?term=mitral+regurgitation&rank=13, Aug. 25, 2008, 1-4.
ClinicalTrials.gov, Pivotal Study of a Percutaneous Mitral Valve Repair System, http://clinicaltrials.gov/ct2/show/NCT00209274?term=mitral+valve&rank=1, Aug. 25, 2008, 1-4.
ClinicalTrials.gov, RESTOR-MV: Randomized Evaluation of a Surgical Treatment for Off-Pump Repair of the Mitral Valve, http://clinicaltrials.gov/ct2/show/NCT00120276?term=myocor&rank=1, Aug. 25, 2008, 1-5.
ClinicalTrials.gov, Safety and Efficacy of the Percutaneous Transvenous Mitral Annuloplasty Device to Reduce Mitral Regurgitation (PTOLEMY), http://clinicaltrials.gov/ct2/show/NCT00568230?term=mitral+valve&rank=53, Aug. 25, 2008, 1-3.
ClinicalTrials.gov, VIVID-Valvular and Ventricular Improvement Via iCoapsys Delivery—Feasibility Study, http://clinicaltrials.gov/ct2/show/NCT00512005?term=mitral+valve&rank=12, Aug. 25, 2008, 1-4.
Crabtree et al., Recurrent Mitral Regurgitation and Risk Factors for Early and Late Mortality After Mitral Valve Repair for Functional Ischemic Mitral Regurgitation, The Society of Thoracic Surgeons , 2008, 1537-43, 85.
Criber et al., Early Experience With Percutaneous Transcatheter Implantation of Heart Valve Prosthesis for the Treatment of End-Stage Inoperable Patients With Calcific Aortic Stenosis, Journal of the American College of Cardiology, Feb. 18, 2004, 698-703, vol. 43, No. 4.
De Bonis et al., Similar long-term results of mitral valve repair for anterior compared with posterior leaflet prolapse, The Journal of Thoracic and Cardiovascular Surgery, Feb. 2006, 364-370, vol. 131, No. 2.
DeLoche et al., Valve repair with Carpentier techniques The second decade, The Journal of Thoracic and Cardiovascular Surgery, Jun. 1990, 990-1002, vol. 99, No. 6.
De Simone et al., A clinical study of annular geometry and dynamics in patients with ischemic mitral regurgitation: new insights into asymmetrical ring annuloplasty, European Journal of Cardio-thoracic Surgery, 2006, 355-361, 29.
Detaint et al., Surgical Correction of Mitral Regurgitation in the Elderly—Outcomes and Recent Improvements, Downloaded from circ.ahajournals.org, Aug. 26, 2008, 265-272.
Dubreuil et al., Percutaneous Mitral Valve Annuloplasty for Ischemic Mitral Regurgitation: First in Man Experience With a Tempory Implant, Catheterization and Cardiovascular Interventions, 2007, 1053-61, 69.
Duffy et al., Feasibility and Short-Term Efficacy of Percutaneous Mitral Annular Reduction for the Therapy of Funcitonal Mitral Regurgitation in Patients With Heart Failure, Catheterization and Cardiovascular Interventions, 2006, 205-210, 68.
Epstein et al., Gross and Microscopic Pathological Changes Associated With Nonthoracotomy Implantable Defibrillator Leads, Downloaded from circ.ahajournals.org, Jul. 23, 2008, 1517-24.
Epstein et al., Embolic Complications Associated With Radiofrequency Catheter Ablation, The American Journal of Cardiology, Mar. 15, 1996, 655-658, vol. 77.
Fagundes et al., Safety of Single Transseptal Puncture for Ablation of Atrial Fibrillation: Retrospective Study from a Large Cohort of Patients, Journal of Cardiovascular Electrophysiology, Dec. 2007, 1277-81, vol. 18, No. 12.
Feldman et al., Patient selection for percutaneous mitral valve repair: insight from early clinical trial applications, Nature Clinical Practice Cardiovascular Medicine, Feb. 2008, 84-90, vol. 5, No. 2.

Feldman et al., Percutaneous Mitral Valve Repair Using the Edge-to-Edge Technique—Six-Month Results of the Everest Phase I Clinical Trial, Journal of the American College of Cardiology, Dec. 6, 2005, 2134-40, vol. 46, No. 11.

Fernandez et al., Early and late-phase events after valve replacement with the St. Jude Medical prosthesis in 1200 patients, The Journal of Thoracic and Cardiovascular Surgery, Feb. 1994, 394-407, vol. 107, No. 2.

Gillinov et al., Durability of Mitral Valve Repair for Degenerative Disease, The Journal of Thoracic and Cardiovascular Surgery, Nov. 1998, 734-743, vol. 116, No. 5.

Grossi et al., Intraoperative Effects of the Coapsys Annuloplasty System in a Randomized Evaluation (RESTOR-MV) of Functional Ischemic Mitral Regurgitation, The Society of Thoracic Surgeons, 2005, 1706-11, 80.

Grossi et al., Late Results of Mitral Valve Reconstruction in the Elderly, The Society of Thoracic Surgeons, 2000, 1224-6, 70.

Grossi et al., Minimally Invasive Mitral Valve Surgery: A 6-Year Experience With 714 Patients, The Society of Thoracic Surgeons, 2002, 660-4, 74.

Hendren et al., Mitral Valve Repair for Ischemic Mitral Insufficiency, The Society of Thoracic Surgeons, 1991, 1246-52, 52.

Heupler et al., Infection Prevention Guidelines for Cardiac Catheterization Laboratories, Catheterization and Cardiovascular Diagnosis, 1992, 260-263, 25.

Hvass et al., Papillary Muscle Sling: A New Functional Approach to Mitral Repair in Patients With Ischemic Left Ventricular Dysfunction and Functional Mitral Regurgitation, The Society of Thoracic Surgeons, 2003, 809-11, 75.

Ibrahim et al., The St. Jude Medical prosthesis—A thirteen-year experience, The Journal of Thoracic and Cardiovascular Surgery, Aug. 1994, 221-230, vol. 108, No. 2.

Iskandar et al., Tricuspid Valve Malfunction and Ventricular Pacemaker Lead: Case Report and Review of the Literature, Echocardiography: A Jrnl of CV Ultrasound & Allied Tech., 2006, 692-697, vol. 23, No. 8.

Kasegawa et al., Mitral Valve Repair for Anterior Leaflet Prolapse With Expanded Polytetrafluoroethylene Sutures, The Society of Thoracic Surgeons, 2006, 1625-31, 81.

Kaye et al., Feasibility and Short-Term Efficacy of Percutaneous Mitral Annular Reduction for the Therapy of Heart Failure-Induced Mitral Regurgitation, Downloaded from circ.ahajournals.org, Aug. 26, 2008, 1795-97.

International Search Report and Written Opinion dated Sep. 22, 2008 issued in PCT Application No. PCT/US08/63560, 11 pages.

International Search Report and Written Opinion dated Sep. 29, 2008 issued in PCT Application No. PCT/US08/63568, 12 pages.

Kerensky, Complications of Cardiac Catheterization and Strategies to Reduce Risks, Diagnostic and Therapeutic Cardiac Catheterization, 1998, Chapter 8, 91-105.

Koertke et al., INR Self-Management Permits Lower Anticoagulation Levels After Mechanical Heart Valve Replacement, downloaded from circ.ahajournals.org, Aug. 26, 2008, II-75-II-78.

Kratz et al., St. Jude Prosthesis for Aortic and Mitral Valve Replacement: A Ten-Year Experience, The Society of Thoracic Surgeons, 1993, 462-8, 56.

Kron et al., Surgical Relocation of the Posterior Papillary Muscle in Chronic Ischemic Mitral Regurgitation, The Society of Thoracic Surgeons, 2002, 600-1, 74.

Kuwahara et al., Mechanism of Recurrent/Persistent Ischemic/Functional Mitral Regurgitation in the Chronic Phase After Surgical Annuloplasty—Importance of Augmented Posterior Leaflet Tethering, Circulation, Jul. 4, 2006, I-529-I-534.

Laskey et al., Multivariable Model for Prediction of Risk of Significant Complication During Diagnostic Cardiac Catheterization, Catheterization and Cardiovascular Diagnosis, 1993, 185-190, 30.

Lee et al., Mitral Valve Reconstruction: Experience Related to Early and Late Mortality and Reoperation, J Heart Valve Dis, Nov. 2005, 715-721, vol. 14, No. 6.

Liddicoat et al., Percutaneous Mitral Valve Repair: A Feasibility Study in an Ovine Model of Acute Ischemic Mitral Regurgitation, Catheterization and Cardiovascular Interventions, 2003, 410-416, 60.

Lim et al., Percutaneous Transthoracic Ventricular Puncture for Diagnostic and Interventional Catheterization, Catheterization and Cardiovascular Interventions, 2008, 915-918, 71.

Lin et al., Severe Symptomatic Tricuspid Valve Regurgitation Due to Permanent Pacemaker or Implantable Cardioverter-Defibrillator Leads, Journal of the American College of Cardiology, May 17, 2005, 1672-5, vol. 45, No. 10.

Lozonschi et al., Transapical Mitral Valved Stent Implantation, The Society of Thoracic Surgeons, 2008, 745-8, 86.

Mack, Percutaneous Therapies for Mitral Regurgitation: Where Do We Stand and Where Are We Going? Do Current Devices Really Represent a Step Forward Compared to Surgery?, 2007 Heart Valve Summit, Jun. 7, 2007, 59 pages.

Maleki et al., Intracardiac Ultrasound Detection of Thrombus on Transseptal Sheath: Incidence, Treatment, and Prevention, Journal of Cardiovascular Electrophysiology, Jun. 2005, 561-565, vol. 16, No. 6.

Maniu et al., Acute and Chronic Reduction of Functional Mitral Regurgitation in Experimental Heart Failure by Percutaneous Mitral Annuloplasty, Journal of the American College of Cardiology, Oct. 19, 2004, 1652-61, vol. 44, No. 8.

McGee et al., Recurrent mitral regurgitation after annuloplasty for functional ischemic mitral regurgitation, Surgery for Acquired Cardiovascular Disease, The Journal of Thoracic and Cardiovascular Surgery, Dec. 2004, 916-924.e4, vol. 128, No. 6.

Mehra et al., Surgery for Severe Mitral Regurgitation and Left Ventricular Failure: What Do We Really Know?, Journal of Cardiac Failure, Mar. 2008, 145-150. vol. 14, No. 2.

Menicanti et al., Functional Ischemic Mitral Regurgitation in Anterior Ventricular Remodeling: Results of Surgical Ventricular Restoration with and Without Mitral Repair, Heart Failure Reviews, 2004, 317-327, 9.

Messas et al., Efficacy of Chordal Cutting to Relieve Chronic Persistent Ischemic Mitral Regurgitation, Circulation, Sep. 9, 2003, II-111-II-115.

Meurin et al., Thromboembolic events early after mitral valve repair: Incidence and predictive factors, International Journal of Cardiology, 2008, 45-52, 126.

Mirable et al., What are the characteristics of patients with severe, symptomatic, mitral regurgitation who are denied surgery?, The European Society of Cardiology, 2007, 1358-65, 28.

Mitchell et al., Complications, Cardiac catheterization and coronary intervention, Chapter 9, 2008, 238-270.

Mishra et al., Coapsys Mitral Annuloplasty for Chronic Functional Ischemic Mitral Regurgitation: 1-Year Results, The Society of Thoracic Surgeons, 2006, 42-46, 81.

Morgan et al., Left Heart Catheterization by Direct Ventricular Puncture: Withstanding the Test of Time, Catheterization and Cardiovascular Diagnosis, 1989, 87-90, 16.

Murday et al., A Prospective Controlled Trial of St. Jude Versus Starr Edwards Aortic and Mitral Valve Prostheses, The Society of Thoracic Surgeons, 2003, 66-74, 76.

Nifong et al., Robotic mitral valve surgery: A United States multicenter trial, The Journal of Thoracic and Cardiovascular Surgery, Jun. 2005, 1395-1404, vol. 129, No. 6.

Noto et al., Cardiac Catheterization 1990: A Report of the Registry of the Society for Cardiac Angiography and Interventions (SCA&I), Catheterization and Cardiovascular Diagnosis, 1991, 75-83, 24.

Ohlow et al., Incidence and outcome of femoral vascular complications among 18,165 patients undergoing cardiac catheterisation, International Journal of Cardiology, 2008, 1-6.

Piazza et al., Transcatheter Mitral Valve Repair for Functional Mitral Regurgitation: Coronary Sinus Approach, Journal of Interventional Cardiology, 2007, 495-508, vol. 20, No. 6.

Pedersen et al., iCoapsys Mitral Valve Repair System: Percutaneous Implantation in an Animal Model, Catheterization and Cardiovascular Interventions, 2008, 125-131, 72.

Prifti et al., Ischemic Mitral Valve Regurgitation Grade II-III: Correction in Patients with Impaired Left Ventricular Function undergoing Simultaneous Coronary Revascularization, J Heart Valve Dis, Nov. 2001, 754-762, vol. 10, No. 6.

Richardson et al., Is a port-access mitral valve repair superior to the sternotomy approach in accelerating postoperative recovery?, Interactive CardioVascular and Thoracic Surgery, Downloaded from icvts.ctsnetjournals.org, Aug. 26, 2008, 670-683, 7.

Ruiz, New Percutaneous Approaches for Mitral Regurgitation, Lenox Hill Heart and Vascular Institute of New York, May 13-16, 2008, 26 pages.

Rumel et al., Section on Cardiovascular Diseases—The Correction of Mitral Insufficiency With a Trans-Valvular Polyvinyl Formalinized Plastic (Ivalon) Sponge Prosthesis, American College of Chest Physicians, Apr. 1958, Downloaded from chestjournal.org, Jul. 23, 2008, 401-413.

Seeburger et al., Minimal invasive mitral valve repair for mitral regurgitation: results of 1339 consecutive patients, European Journal of Cardio-thoracic Surgery, 2008, 1-6.

Southard et al., Current Catheter-Based Treatments of Functional Mitral Regurgitation, Cardiac Interventions Today, Jun. 2007, 41-44.

Svensson et al., United States Feasibility Study of Transcatheter Insertion of a Stented Aortic Valve by the Left Ventricular Apex, The Society of Thoracic Surgeons, 2008, 46-55, 86.

Toledano et al., Mitral regurgitation: Determinants for referral for cardiac surgery by Canadian cardiologists, Can J. Cardiol, Mar. 1, 2007, 209-214, vol. 23, No. 3.

Tops et al., Percutaneous Valve Procedures: An Update, Curr Probl Cardiol, Aug. 2008, 417-426.

Walther et al., Transapical minimally invasive aortic valve implantation; the initial 50 patients, European Journal of Cardio-thoracic Surgery, 2008, 983-988, 33.

Webb et al., Percutaneous Mitral Annuloplasty With the MONARC System: Preliminary Results From the EVOLUTION Trial, TCT-103, The American Journal of Cardiology, Oct. 22-27, 2006, 49M.

Webb et al., Percutaneous Transvenous Mitral Annuloplasty—Initial Human Experience with Device Implantation in the Coronary Sinus, downloaded from circ.ahajournals.org, Aug. 26, 2008, 851-855.

Webster et al., Impact of transvenous ventricular pacing leads on tricuspid regurgitation in pediatric and congenital heart disease patients, J Interv Card Electrophysiol, 2008, 65-68, 21.

Ye et al., Six-month outcome of transapical transcatheter aortic valve implantation in the initial seven patients, European Journal of Cardio-thoracic Surgery, 2007, 16-21, 31.

Yoshida, et al., Assessment of Left-to-Right Atrial Shunting After Percutaneous Mitral Valvuloplasty by Transesophageal Color Doppler Flow-Mapping, Circulation, Dec. 1989, 1521-1526, vol. 80, No. 6.

Zhou et al., Thromboembolic Complications of Cardiac Radiofrequency Catheter Ablation: A Review of the Reported Incidence, Pathogenesis and Current Research Directions, Journal of Cardiovascular Electrophysiology, Apr. 1999, 611-620, vol. 10, No. 4.

U.S. Office Action dated Jul. 8, 2009 issued in U.S. Appl. No. 11/258,828, 7 pages.

International Search Report and Written Opinion dated Aug. 11, 2009 issued in PCT Application No. PCT/US2009/046995, 11 pages.

U.S. Office Action dated Sep. 29, 2009 issued in U.S. Appl. No. 12/209,686, 9 pages.

European Search Report dated Jul. 12, 1984 cited in EP0125393.

"French catheter scale chart" http://en.wikipedia.org/wiki/French_catheter_scale_chart, Dec. 20, 2006, 1 page.

"General Physical Properties of PVA Sponge (values are not guaranteed)", Ceiba Technologies, http://www.ceibatech.com/PVASpongeDate.htm, Dec. 20, 2006 3 pages.

"PVA Datasheet", www.sponge-pva.com/data.htm, Dec. 20, 2006, 2 pages.

"PVA Sponge W (wet) & D (dry)", Ceiba Technologies, http://www.ceibatech.com/PVASpongeW&D.htm, Dec. 20, 2007 5 pages.

SPI-Chem™ Vinylec® (Formvar®) Resins, http://www.2spi.com/catalog/submat/formvar-resins.shtml, Dec. 20, 2006, 5 pages.

"Vinylec® Resins", http://www.2spi.com/catalog/submat/vinylec-physical.html, Dec. 20, 2006, 1 page.

U.S. Office Action dated Dec. 15, 2009 issued in U.S. Appl. No. 11/258,828, 12 pages.

U.S. Office Action dated Jan. 8, 2010 issued in U.S. Appl. No. 11/748,147, 63 pages.

U.S. Office Action dated Jan. 14, 2010 issued in U.S. Appl. No. 11/940,674, 59 pages.

U.S. Office Action dated Feb. 4, 2010 issued in U.S. Appl. No. 11/748,138, 58 pages.

U.S. Office Action dated Jun. 2, 2010 issued in U.S. Appl. No. 12/209,686, 15 pages.

U.S. Office Action dated Jun. 28, 2010 issued in U.S. Appl. No. 11/258,828, 14 pages.

Notice of Allowance dated Jul. 1, 2010 issued in U.S. Appl. No. 11/940,674, 6 pages.

U.S. Office Action dated Jul. 20, 2010 issued in U.S. Appl. No. 11/748,147, 15 pages.

Ryhänen et al., In vivo biocompatibility evaluation of nickel-titanium shape memory metal alloy: Muscle and perineural tissue responses and encapsule membrane thickness, Muscle and Perineural Tissue Response to Nitinol, Jan. 19, 1998, pp. 481-488.

International Search Report and Written Opinion dated Jul. 6, 2010 issued in PCT Patent Application No. PCT/US2010/032764, 9 pages.

Extended European search report dated Nov. 30, 2010 issued in European Patent Application No. 08850467.5, 6 pages.

Extended European search report dated Nov. 30, 2010 issued in European Patent Application No. 08755418.4, 7 pages.

Extended European search report dated Nov. 30, 2010 issued in European Patent Application No. 08849442.2, 6 pages.

U.S. Office Action dated Aug. 30, 2010 issued in U.S. Appl. No. 11/748,138, 9 pages.

International Search Report and Written Opinion dated Sep. 21, 2010 issued in PCT Patent Application No. PCT/US2010/043360, 9 pages.

Extended European Search Report dated Dec. 1, 2010 issued in European Patent Application No. 08755426.7, 6 pages.

Extended European Search Report dated Dec. 14, 2010 issued in European Patent Application No. 06816336.9, 7 pages.

U.S. Office Action dated Mar. 21, 2011 issued in U.S. Appl. No. 11/258,828, 22 pages.

U.S. Office Action dated Apr. 4, 2011 issued in U.S. Appl. No. 11/940,724, 65 pages.

European Examination Report dated Aug. 4, 2011 issued in European Patent No. 06 816 336.9, 3 pages.

U.S. Office Action dated Aug. 29, 2011 issued in U.S. Appl. No. 11/940,694, 11 pages.

European Examination Report dated Aug. 11, 2011 issued in European Patent No. 08 755 418.4, 3 pages.

Notice of Allowance dated Oct. 31, 2011 issued in U.S. Appl. No. 11/258,828, 10 pages.

Preliminary Report on Patentability dated Nov. 1, 2011 issued in PCT Patent Application No. PCT/US2010/032764, 4 pages.

U.S. Office Action dated Nov. 3, 2011 issued in U.S. Appl. No. 12/872,228, 8 pages.

Notice of Allowance dated Dec. 14, 2011 issued in U.S. Appl. No. 12/431,399, 12 pages.

U.S. Office Action dated Jan. 18, 2012 issued in U.S. Appl. No. 11/940,724, 10 pages.

International Preliminary Report on Patentability dated Jan. 31, 2012 issued in PCT Patent Application No. PCT/US2010/043360, 7 pages.

U.S. Office Action dated Feb. 15, 2012 issued in U.S. Appl. No. 11/940,694, 9 pages.

U.S. Notice of Allowance dated Mar. 8, 2012 issued in U.S. Appl. No. 12/872,228, 7 pages.

U.S. Office Action dated Jun. 20, 2012 issued in U.S. Appl. No. 11/940,694, 9 pages.

U.S. Office Action dated Jun. 21, 2012 issued in U.S. Appl. No. 11/748,147, 29 pages.

Balzer et al, Real-time transesophageal three-dimensional echocardiography for guidance of percutaneous cardiac interventions: first experience, Clinical Research in Cardiology, May 29, 2008, 565-574, vol. 97, No. 9.

Clinical Trials.gov, Safety and Efficacy Study of the PTMA Device to Reduce Mitral Valve Regurgitation in Patients With Heart Failure (PTOLEMY2Canada), http://clinicaltrials.gov/ct2/show/study/NCT00815386?term=Viacor&rank=3, 1-3, Dec. 2008.

Clinical Trials.gov, Study of Safety and Efficacy of the Percutaneous Reduction of Mitral Valve Regurgitation in Heart Failure Patients (PTOLEMY-2), http://clinicaltrials.gov/ct2/show/NCT00787293?term=Viacor&rank=5, 1-2, Nov. 2008.

Corbisiero et al., Does Size Really Matter? A Comparison of the Riata Lead Family Based on Size and Its Relation to Performance, Pace, Jun. 2008, vol. 31, 722-726.
Criber et al., Treatment of Calcific Aortic Stenosis With the Percutaneous Heart Valve—Mid-Term Follow-Up From The Initial Feasibility Studies: The French Experience, Journal of the American College of Cardiology, Mar. 21, 2006, vol. 47, No. 6, 1241-1223.
Danik et al., Timing of delayed perforation with the St. Jude Riata lead: A single-center experience and a review of the literature, Heart Rhythm Society, Dec. 2008, vol. 5, No. 12, 1667-1672.
Del Valle-Fernández et al., Transcatheter heart valves for the treatment of aortic stenosis: state-of-the-art, Minerva Cardioangiologica, Oct. 2008, vol. 56, No. 5, 543-556.
Douthitt, Cardiac Dimensions® Inc. Receives CE Mark for CARILLON™ Mitral Contour System™, Cardiac.Dimensions—News, htpp://www.cardiacdimensions.com/usa/press-release-2-4-09.html, downloaded Feb. 24, 2009, 1-2.
Dvorin, Endovalve Inc., Pioneering percutaneous mitral valve replacement., Start-Up Windhover's Review of Emerging Medical Ventures, Jun./Jul. 2006, vol. 11, No. 7, 1-2.
Eltchaninoff, Clinical results of percutaneous aortic valve implantation, Euro PCR07, Cribier-Edwards, 30 pages. 2007.
Evalve reports 1st MitraClip treatments in the Netherlands, Medical Device Daily, Feb. 19, 2009, vol. 13, No. 32, 2 pages.
A first for MiCardia's Dynoplasty, Medical Device Daily, Feb. 19, 2009, vol. 13, No. 32, 1 page.
Fitts et al , Fluoroscopy-Guided Femoral Artery Puncture Reduces the Risk of PCI-Related Vascular Complications, Journal of Interventional Cardiology, vol. 21, No. 3, 2008, 273-278.
Gelsomino et al., Left ventricular diastolic function after restrictive mitral ring annuloplasty in chronic ischemic mitral regurgitation and its predictive value on outcome and recurrence of regurgitation, International Journal of Cardiology, vol. 132, 2009, 419-428.
Geyfman et al., Cardiac Tamponade as Complication of Active-Fixation Atrial Lead Perforations: Proposed Mechanism and Management Algorithm, PACE, Apr. 2007, vol. 30, 498-501.
Gorman et al., Surgical Therapy for Mitral Regurgitation: The Key to Preventing Heart Failure?, Prevention of Heart Failure After Myocardial Infarction, 2008, 211-215.
Harper, Evalve Announces Enrollment Completion of the Everest Randomized Study, http://www.evalveinc.com/europe/press/17.html, downloaded Feb. 24, 2009, 1-3.
Harper, Two-Year Follow-Up Data Demonstrates Preservation of Adequate Mitral Valve Area in Patients Treated with the MitraClip®-system, http://www.evalveinc.com/europe/press/21.html, downloaded Feb. 24, 2009, 1-3.
Hung et al., 3D Echocardiography: A Review of the Current Status and Future Directions, ASE Position Paper, Journal of the American Society of Echocardiography, Mar. 2007, 213-233.
Hung et al., Mechanism of Dynamic Regurgitant Orifice Area Variation of Functional Mitral Regurgitation—Physiologic Insights From the Proximal Flow Convergence Technique, Journal of the American College of Cardiology, Feb. 1999, vol. 33, No. 2, 538-545.
Hung et al., A Novel Approach for Reducing Ischemic Mitral Regurgitation by Injection of a Polymer of Reverse Remodel and Reposition Displaced Papillary Muscles, Circulation—Journal of the American Heart Association, Sep. 30, 2008, Downloaded from circ.ahajournals.org at National Insthealth Lib on Feb. 25, 2009, S262-S269.
Hytowitz, First U.S. Patients Enrolled in the Realism Continued Access Study, evalve, http://www.evalveinc.com/europe/pressl22/html, downloaded Feb. 24, 2009, 2 pages.
International Search Report and Written Opinion dated Feb. 25, 2009 issued in PCT Application No. PCT/US08183570, 13 pages.
International Search Report and Written Opinion dated Apr. 2, 2009 issued in PCT Application No. PCT/US08/83574, 8 pages.
Jilaihawi et al., Percutaneous Aortic Valve Replacement in Patients with Challenging Aortoiliofemoral Access, Catheterization and Cardiovascular Interventions, 2008, vol. 72, 885-890.
Jovin et al., Atrial Fibrillation and Mitral Valve Repair, Pace, Aug. 2008, vol. 31, 1057-1063.
Kahlert et al., Direct Assessment of Size and Shape of Noncircular Vena Contracta Area in Functional Versus Organic Mitral Regurgitation Using Real-Time Three-Dimensional Echocardiography, Valvular Heart Disease, Journal of the American Society of Echocardiography, Aug. 2008, vol. 21, No. 8, 912-921.
Kempfert et al., Minimally invasive off-pump valve-in-a-valve implantation: the atrial transcatheter approach for re-operative mitral valve replacement, European Heart Journal, 2008, vol. 29, 2382-2387.
Kerensky, Complications of Cardiac Catheterization and Strategies to Reduce Risks, Diagnostic and Therapeutic Cardiac Catheterization—Third Edition—Chapter 8, 1998, 17 pages.
Kodali et al., Transcatheter Valve Repair and Replacement, Downloaded from arjournals.annualreviews.org by National Institute of Health Library on Feb. 25, 2009, 14 pages.
Kwan et al., Geometric Differences of the Mitral Apparatus Between Ischemic and Dilated Cardiomyopathy With Significant Mitral Regurgitation—Real-Time Three-Dimensional Echocardiography Study, Circulation, Mar. 4, 2003, 1135-1140.
Leung et al., Percutaneous Mitral Valve Repair—An overview of the current devices and techniques, Coronory/Cardiac Interventions—Endovascular Today, Oct. 2006, 26-33.
Levine et al., Mechanistic Insights into Functional Mitral Regurgitation, Valvular Heart Disease, 2009, 125-129.
Little et al., Three-Dimensional Ultrasound Imaging Model of Mitral Valve Regurgitation: Design and Evaluation, Ultrasound in Medicine and Biology, 2008, vol. 34, No. 4, 647-654.
Llaneras et al., Large Animal Model of Ischemic Mitral Regurgitation, The Society of Thoracic Surgeons—Ischemic Mitral Insufficiency, 1994, vol. 57, 432-439.
Magne et al., Ischemic Mitral Regurgitation: A Complex Multifaceted Disease, Cardiology, 2009, vol. 112, 244-259.
McClure et al., Early and late outcomes in minimally invasive mitral valve repair: An eleven-year experience in 707 patients, Acquired Cardiovascular Disease, The Journal of Thoracic and Cardiovascular Surgery, Jan. 2009, vol. 137, No. 1, 70-75.
Modi et al., Minimally invasive mitral valve surgery: a systematic review and meta-analysis, European Journal of Cardio-Thoracic Surgery, 2008, vol. 34, 943-952.
Myers, Jr., et al., Color Doppler Velocity Accuracy Proximal to Regurgitant Orifices: Influence of Orifice Aspect Ratio, Ultrasound in Medicine and Biology, 1999, vol. 25, No. 5, 771-792.
Ning et al., Live three-dimensional transesophageal echocardiography in mitral valve surgery, Chinese Medical Journal, 2008, vol. 121, No. 20, 2037-2041.
Nötzold et al., Microemboli in aortic valve replacement, Future Drugs Ltd, Expert Rev. Cardiovasc. Ther., vol. 4, No. 6, 2006, 853-859.
Onundarson et al., Warfarin anticoagulation intensity in specialist-based and in computer-assisted closing practice, International Journal of Laboratory Hematology, 2008, vol. 30, 382-389.
Otsuji et al., Insights From Three-Dimensional Echocardiography Into the Mechanism of Functional Mitral Regurgitation—Direct In Vivo Demonstration of Altered Leaflet Tethering Geometry, Circulation, Sep. 16, 1997, vol. 96, No. 6, 1999-2008.
Fukuda et al, Maintenance of Geometric Alterations Associated with Percutaneous Mitral Valve Repair: Real-Time Three-Dimensional Echocardiographic Assessment in an Ovine Model, J. Heart Valve Dis, May 2008, vol. 17, No. 3, 276-282.
Pai et al., Effect of Atrial Fibrillation on the Dynamics of Mitral Annular Area, J. Heart Valve Dis., Jan. 2003, vol. 12, No. 1, 31-37.
Palacios et al., Safety and Feasibility of Acute Percutaneous Septal Sinus Shortening: First-In-Human Experience, Catheterization and Cardiovascular Interventions, 2007, vol. 69, 513-518.
Paniagua et al., First Human Case of Retrograde Transcatheter Implantation of an Aortic Valve Prosthesis, Texas Heart Institute Journal, Transcatheter Aortic Valve Prosthesis, 2005, vol. 32, No. 3, 393-398.
Rodés-Cabau et al., Feasibility and Initial Results of Percutaneous Aortic Valve Implantation Including Selection of the Transfemoral or Transapical Approach in Patients With Severe Aortic Stenosis, The American Journal of Cardiology, 2008, 1240-1246.

Satpathy et al., Delayed Defibrillator Lead Perforation: An Increasing Phenomenon, Pace, Jan. 2008, vol. 31, 10-12.
Schofer, Percutaneous MVR: Clinical Evaluation—The Carillon Experience, EuroPCR 2007, Barcelona, Spain, May 22-25, 2007, 35 pages.
Schwammenthal et al., Dynamics of Mitral Regurgitant Flow and Orifice Area—Physiologic Application of the Proximal Flow Convergence Method: Clinical Data and Experimental Testing, Circulation, Jul. 1994, vol. 90, No. 1, 307-322.
Spencer, Viacor, Inc. Announces First Patient Treated in PTOLEMY-2 Study, http://www.viacorinc.com/viacor_news.html, Nov. 14, 2008, downloaded Feb. 24, 2009, 2 pages.
Sterliński et al., Subacute cardiac perforations associated with active fixation leads, Clinical Research Leads and Lead Extraction, Europace, 2009, vol. 11, 206-212.
Turakhia et al., Rates and severity of perforation from implantable cardioverter-defibrillator leads: A 4-year study, J Interv Card Electrophysiol, 2009, vol. 24, 47-52.
Vahanian, The Cardiologist's Perspective on the Future of Percutaneous Mitral Valve Repair, Euro PCR07, 53 pages, 2007.
Vahanian, Coronary Sinus and Direct Annuloplasty Percutaneous Mitral Valve Repair, Innovations in Cardiovascular Interventions, Dec. 7-9, 2008, Tel-Aviv, Israel, 45 pages.
Vahanian, Edwards Monarc system—Evolution Interim Results, 31 pages, 2007.
Vahanian, Overview on Percutaneous Mitral Valve Technology, Euro PCR07, Transcatheter Valve Symposium, Barcelona, May 22-25, 2007, 29 pages.
Van Gelder et al., Diagnosis and Management of Inadvertently Placed Pacing and ICD Leads in the Left Ventricle: A Multicenter Experience and Review of the Literature, Pace, May 2000, vol. 23, 877-883.
Vranckx et al., The TandemHeart®, percutaneous transseptal left ventricular assist device: a safeguard in high-risk percutaneous coronary interventions. The six-year Rotterdam experience, Clinical research EuroInterv., 2008, vol. 4, 331-337.
Wolf et al., Solid and gaseous cerebral micorembolization after biologic and mechanical aortic valve replacement: Investigation with multirange and multifrequency transcranial Doppler ultrasound, The Journal of Thoracic and Cardiovascular Surgery, Mar. 2008, vol. 135, No. 3, 512-520.
Xiangming et al., In Vivo Characterization of Attachment Safety Between Cardiac Pacing Lead and Canine Heart Muscle*, Acta Mechanica Solida Sinica, Sep. 2007, vol. 20, No. 3, 189-197.
Yamaura et al., Geometrical Demonstration and Three-Dimensional Quantitative Analysis of the Mitral Valve With Real-Time Three-Dimensional Echocardiography: Novel Anatomical Image Creation System, J Echocardiogr, 2004, vol. 2, No. 4, 99-104.
Yosefy et al., Proximal Flow Convergence Region as Assessed by Real-time 3-Dimensional Echocardiography: Challenging the Hemispheric Assumption, Journal of the American Society of Echocardiography, Apr. 2007, vol., No. 4, 389-396.
U.S. Office Action dated Sep. 19, 2012, issued in U.S. Appl. No. 12/510,929, 10 pages.
U.S. Office Action dated Oct. 9, 2012, issued in U.S. Appl. No. 12/872,228, 7 pages.
Balzer et al., Real-time transesophageal three-dimensional echocardiography for guidance of percutaneous cardiac interventions: first experience, Clinical Research in Cardiology, May 29, 2008, 565-574, vol. 97, No. 9.
Carlson et al., Lead Perforation: Incidence in Registries, Pace Industry Viewpoint, Jan. 2008, 13-15, vol. 31.
Clinical Trials.gov, Comparing the Effectiveness of a Mitral Valve Repair Procedure in Combination With Coronary Artery Bypass Grafting (CABG) Versus CABG Alone in People with Moderate Ischemic Mitral Regurgitation, http://clinicaltrials.gov/ct2/show/record/NCT00806988?term=mitral+repair&rank=7, Feb. 24, 2009, 1-3.
Clinical Trials.gov, Safety and Efficacy Study of the PTMA Device to Reduce Mitral Valve Regurgitation in Patients With Heart Failure (PTOLEMY2Canada), http://clinicaltrials.gov/ct2/show/study/NCT00815386?term=Viacor&rank=3, 1-3.
Clinical Trials.gov, Study of Safety and Efficacy of the Percutaneous Reduction of Mitral Valve Regurgitation in Heart Failure Patients (PTOLEMY-2), http://clinicaltrials.gov/ct2/show/NCT00787293?term=Viacor&rank=5, 1-2.
Cohen, Trans-Septal Technique for Tandemheart Insertion, Lenox Hill Heart and Vascular Institute of New York, Barcelona May 22-25, 2007, 18 pages.
European Intent to Grant dated Feb. 22, 2013 issued in European Patent Application No. 08 755 418.4, 7 pages.
European Search Report dated Mar. 6, 2013 issued in European Patent Application No. 10804952.9, 8 pages.
Notice of Allowance dated Mar. 8, 2013 issued in U.S. Appl. No. 11/748,138, 9 pages.
Final Office Action dated Mar. 13, 2013 issued in U.S. Appl. No. 11/748,147, 10 pages.
Final Office Action dated Mar. 22, 2013 issued in U.S. Appl. No. 12/510,929, 13 pages.
Notice of Allowance dated Apr. 11, 2013 issued in U.S. Appl. No. 13/545,927, 12 pages.

* cited by examiner

BALLOON MITRAL SPACER

CROSS-REFERENCE TO RELATED APPLICATION

The subject application is a continuation-in-part of U.S. patent application Ser. No. 11/258,828 now U.S. Pat. No. 8,092,525, entitled "Heart Valve Implant" filed on Oct. 26, 2005, which is hereby incorporated by reference.

FIELD

The present disclosure relates to the repair and/or correction of dysfunctional heart valves, and more particularly pertains to heart valve implants and systems and methods for delivery and implementation of the same.

BACKGROUND

A human heart has four chambers, the left and right atrium and the left and right ventricles. The chambers of the heart alternately expand and contract to pump blood through the vessels of the body. The cycle of the heart includes the simultaneous contraction of the left and right atria, passing blood from the atria to the left and right ventricles. The left and right ventricles then simultaneously contract forcing blood from the heart and through the vessels of the body. In addition to the four chambers, the heart also includes a check valve at the upstream end of each chamber to ensure that blood flows in the correct direction through the body as the heart chambers expand and contract. These valves may become damaged, or otherwise fail to function properly, resulting in their inability to properly close when the downstream chamber contracts. Failure of the valves to properly close may allow blood to flow backward through the valve resulting in decreased blood flow and lower blood pressure.

Mitral regurgitation is a common variety of heart valve dysfunction or insufficiency. Mitral regurgitation occurs when the mitral valve separating the left coronary atrium and the left ventricle fails to properly close. As a result, upon contraction of the left ventricle blood may leak or flow from the left ventricle back into the left atrium, rather than being forced through the aorta. Any disorder that weakens or damages the mitral valve can prevent it from closing properly, thereby causing leakage or regurgitation. Mitral regurgitation is considered to be chronic when the condition persists rather than occurring for only a short period of time.

Regardless of the cause, mitral regurgitation may result in a decrease in blood flow through the body (cardiac output). Correction of mitral regurgitation typically requires surgical intervention. Surgical valve repair or replacement may be carried out as an open heart procedure. The repair or replacement surgery may last in the range of about three to five hours, and may be carried out with the patient under general anesthesia. The nature of the surgical procedure requires the patient to be placed on a heart-lung machine. Because of the severity/complexity/danger associated with open heart surgical procedures, corrective surgery for mitral regurgitation is typically not recommended until the patient's ejection fraction drops below 60% and/or the left ventricle is larger than 45 mm at rest.

BRIEF DESCRIPTION OF THE DRAWINGS

Features and advantage of the claimed subject matter will be apparent from the following description of embodiments consistent therewith, which description should be considered in conjunction with the accompanying drawings, wherein:

FIG. 8 shows an embodiment of a mitral valve implant including a barb anchor portion consistent with the present disclosure;

DESCRIPTION

The present disclosure relates to a heart valve implant. A heart valve implant herein may suitably be used in connection with the treatment and/or correction of a dysfunctional or inoperative heart valve. One suitable implementation for a heart valve implant consistent with the present disclosure is the treatment of mitral valve regurgitation. For the ease of explanation, the heart valve implant herein is described in terms of a mitral valve implant, such as may be used in treating mitral valve regurgitation. However, a heart valve implant consistent with the present disclosure may be employed for treating and/or correcting other dysfunctional or inoperative heart valves. The present disclosure should not, therefore, be construed as being limited to use as a mitral valve implant.

Generally, a heart valve implant consistent with the present disclosure may interact with at least a portion of an existing heart valve to prevent and/or reduce regurgitation. For example, at least a portion of one or more cusps of the heart valve may interact with, engage, and/or seal against at least a portion of the heart valve implant when the heart valve is in a closed condition. The interaction, engagement and/or sealing between at least a portion of at least one cusp and at least a portion of the heart valve implant may reduce and/or eliminate regurgitation in a heart valve, for example, providing insufficient sealing, including only a single cusp, e.g., following removal of a diseased and/or damaged cusp, and/or having a ruptured cordae. A heart valve implant consistent with the present disclosure may be used in connection with various additional and/or alternative defects and/or deficiencies.

Figure 1:
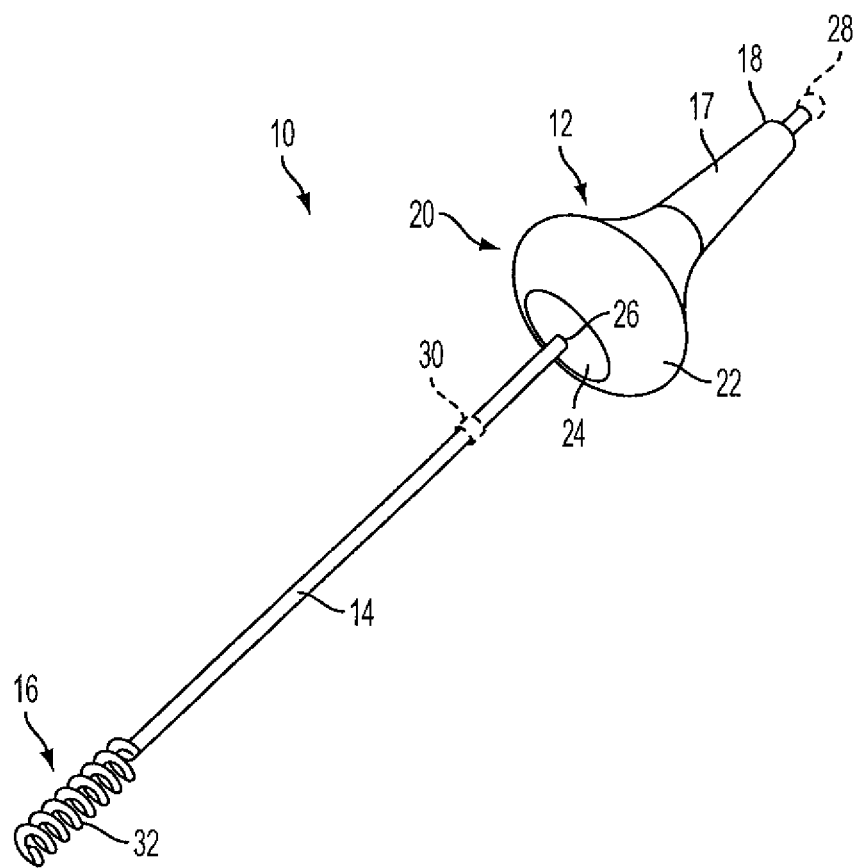
FIG. 1 is a perspective view of an embodiment of a mitral valve implant consistent with the present disclosure.

Referring to FIG. 1, a perspective view of an embodiment of a mitral valve implant 10 is depicted. In general, the mitral valve implant 10 may be capable of increasing the sealing and/or closure of the passage between the left ventricle and the left atrium during contraction of the left ventricle relative to damaged and/or leaking native valve. Accordingly, in some embodiments the mitral valve implant 10 may be capable of operating in combination with a partially operable and/or damaged mitral valve. That is, the mitral valve implant may interact and/or cooperate with at least a portion of the native mitral valve to reduce and/or eliminate excessive regurgitation. As shown, mitral valve implant may generally include a valve body portion 12 which may be coupled to a shaft 14. The shaft 14 may be coupled to an anchor portion 16.

The valve body portion 12 of the mitral valve implant 10 shown in FIG. 1 may have a generally tapered shape, including a sidewall 17 tapering outwardly from a narrow portion 18 adjacent to one end of the valve body 12 to an enlarged portion 20 adjacent to the other end of the valve body 12. The taper of the sidewall 17 may have a flared or belled shape, providing an at least partially concave geometry, as depicted in FIG. 1. In various other embodiments the valve body may include a sidewall having a generally uniform taper, providing a straight profile. In still other embodiments, the sidewall of the valve body may exhibit a convex taper, producing an at least somewhat bulging tapered profile.

The enlarged portion 20 of the valve body 12 may have an arcuate profile around the circumference 22 of the proximal region of the enlarged portion 20. The bottom 24 of the enlarged portion 20 may be provided having a flat and/or arcuate shape. Furthermore, the bottom 24 of the proximal region may include convex and/or concave contours.

According to an embodiment, the valve body 12 may be slidably coupled to the shaft 14. The valve body 12 may include an opening 26 extending from the bottom 24 of the enlarged portion 20, through the valve body 12, and to the narrow portion 18. In one such embodiment, the opening 26 may extend generally axially through the valve body 12. The opening 26 may be sized to slidably receive at least a portion of the shaft 14 therethrough. The shaft 14 may include one or more stops 28, 30. The stops 28, 30 may be sized and/or shaped to control and/or restrict translation of the valve body 12 along the shaft 14 beyond the respective stops 28, 30. In this manner, in the illustrated embodiment, translation of the valve body 12 along the shaft 14 may be restricted to the expanse of the shaft 14 between the stops 28, 30.

One or more of the stops 28, 30 may be integrally formed with the shaft 14. Furthermore, one or more of the stops 28, 30 may be provided as a separate member coupled to and/or formed on the shaft 14. In an embodiment in which one or more of the stops 28, 30 are integrally formed with the shaft 14, the valve body 12 may be slidably coupled to the shaft 14 by pressing the valve body 12 over at least one of the stops 28, 30, which may at least partially elastically deform the opening 26 to permit passage of at least one of the stops 28, 30. Once the one or more of the stops 28, 30 have been pressed through the opening 26, the opening 26 may at least partially elastically recover, thereby resisting passage of the one or more stops 28, 30 back through the opening 26. Various other arrangements may be employed for providing stops on the shaft and/or for controlling and/or limiting translation of the valve body along the shaft.

The anchor portion 16 may include a helical member 32 coupled to the shaft 14. As shown, the helical member 32 may be loosely wound such that adjacent turns of the helical member 32 do not contact one another, for example resembling a corkscrew-type configuration. The anchor portion 16 may be engaged with tissue by rotating the anchor portion 16 about the axis of the helical member 32, thereby advancing the anchor portion 16 into tissue. Consistent with such an embodiment, the anchor portion 16 may resist pulling out from the tissue. The anchor portion 16 may be provided as an extension of the shaft 14 wound in a helical configuration. Consistent with related embodiments, the anchor portion 16 may be formed as a separate feature and may be coupled to the shaft 14, e.g., using mechanical fasteners, welding, adhesive, etc.

According to various alternative embodiments, the anchor portion may include various configurations capable of being coupled to and/or otherwise attached to native coronary tissue. For example, the anchor portion may include one or more prongs adapted to pierce coronary tissue and to alone, or in conjunction with other features, resist removal of the anchor portion from tissue. For example, the anchor portion may include a plurality of prongs which may engage native coronary tissue. According to various other embodiments, the anchor portion may include features that may facilitate attachment by suturing. Exemplary features to facilitate suturing may include rings or openings, suture penetrable tabs, etc. Various other anchor portions that may allow attachment or coupling to native coronary tissue may also suitably be employed in connection with the present disclosure.

Figure 2:
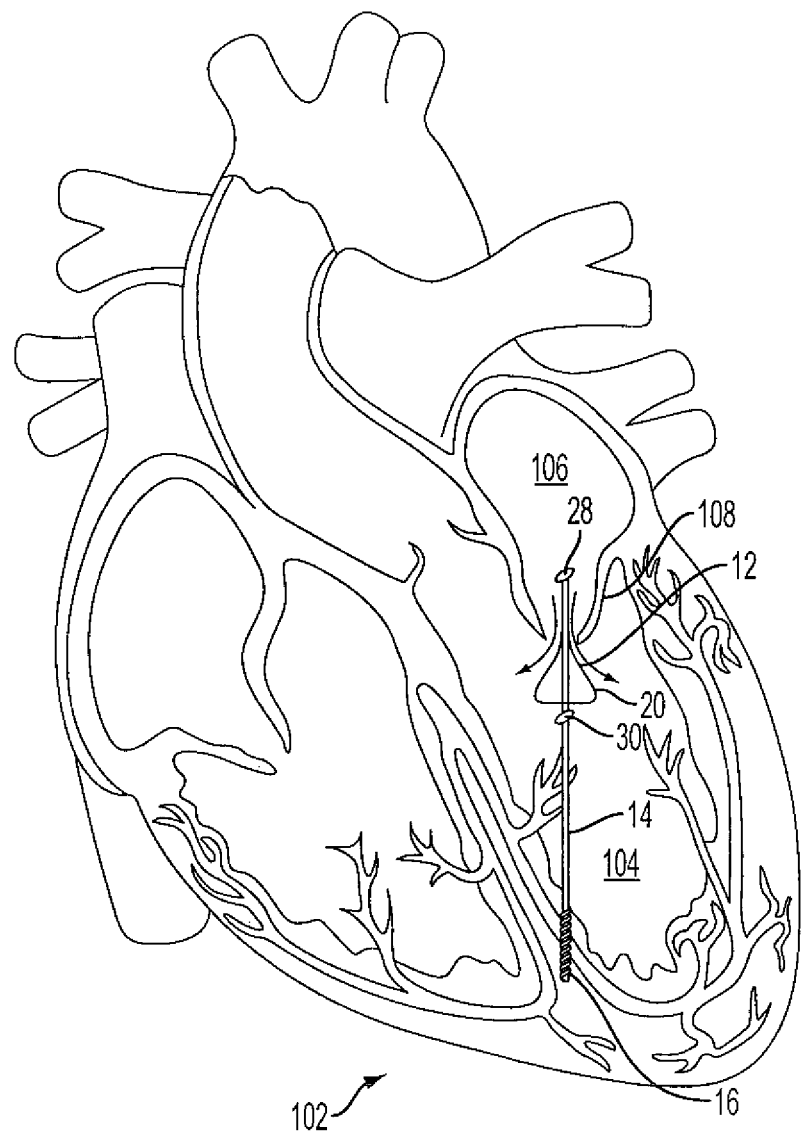
FIG. 2 depicts an embodiment mitral valve implant consistent with the present disclosure implanted within a heart in an open position.
Figure 3:
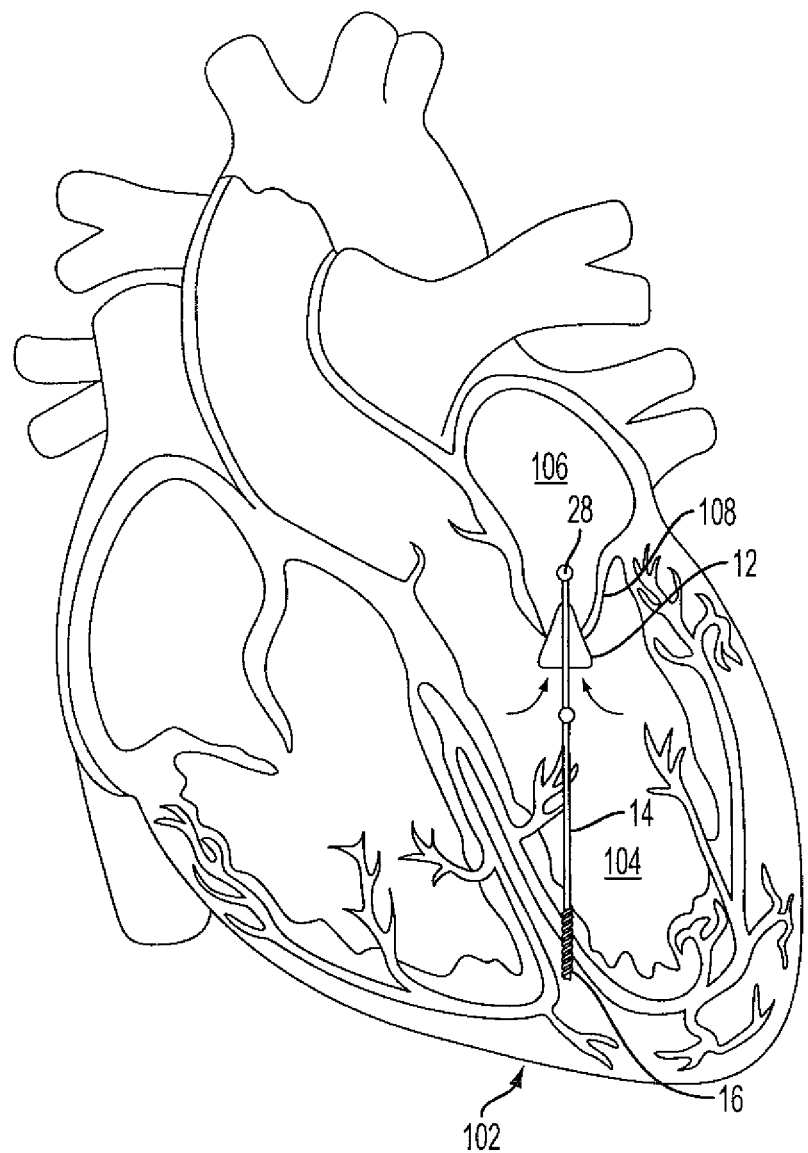
FIG. 3 depicts an embodiment of a mitral valve implant consistent with the present disclosure implanted within a heart in a closed position.

Turning to FIGS. 2 and 3, the mitral valve implant 10 is shown implanted within a heart 102. The mitral valve implant 10 may be disposed at least partially within the left ventricle 104 of the heart 102. As shown, the anchor portion 16 may be engaged with native coronary tissue within and/or adjacent to the left ventricle 104. The shaft 14, coupled to the anchor portion 16, may extend into the left ventricle 104. The shaft 14 may further extend at least partially within the mitral valve 108, i.e., the shaft may extend at least partially between the cusps of the mitral valve, and may also extend at least partially into the left atrium 106. The valve body 12 of the mitral valve implant 10 may be positioned at least partially within the left ventricle 104 with the enlarged portion 20 within the left ventricle 104 and with the narrow portion 18 positioned at least partially within and/or pointed towards the left atrium 106.

FIG. 2 depicts the heart 102 in a condition in which the pressure of blood within the left atrium 106 is at equal to, or higher than, the pressure of blood within the left ventricle 104, e.g., during contraction of the left atrium 106. As shown, when the pressure of blood within the left atrium 106 is greater than or equal to the pressure of blood within the left ventricle 104, blood may flow from the left atrium 106 into the left ventricle 104. The pressure differential and/or the flow of blood from the left atrium 106 to the left ventricle 104 may slidably translate the valve body 12 along the shaft 14 toward the left ventricle 104, in the direction of blood flow between the chambers.

Sliding translation of the valve body 12 along the shaft 14 may at least partially withdraw the valve body 12 from the mitral valve 108 to an open position, as shown. When the valve body is at least partially withdrawn from the mitral valve 108, a passage may be opened between the valve body 12 and the mitral valve 108, allowing blood to flow from the left atrium 106 to the left ventricle 104. Translation of the valve body 12 away from the mitral valve 108 may be controlled and/or limited by the stop 30. In the open position, the stop 30 may maintain the valve body 12 in general proximity to the mitral valve 108 while still permitting sufficient clearance between the mitral valve 108 and the valve body 12 to permit adequate blood flow from the left atrium 106 to the left ventricle 104. Additionally, the flow of blood from left atrium to the left ventricle may cause the mitral valve to flare and/or expand outwardly away from the mitral valve implant, permitting blood flow between the implant and the cusps of the mitral valve.

As the left ventricle 104 contracts, the pressure of blood in the left ventricle 104 may increase such that the blood pressure in the left ventricle 104 is greater than the blood pressure in the left atrium 106. Additionally, as the pressure of the blood in the left ventricle 104 initially increases above the pressure of the blood in the left atrium 106, blood may begin to flow towards and/or back into the left atrium 106. The pressure differential and/or initial flow of blood from the left ventricle 104 into the left atrium 106 may act against the valve body 12 and may translate the valve body 12 toward the left atrium 104. For example, pressurized blood within the left ventricle 104 may act against the bottom 24 of the valve body 12 inducing sliding translation of the valve body 12 along the shaft 14 toward the left atrium 106.

Turning to FIG. 3, the mitral valve implant 10 is shown in a closed position. In the closed position the valve body 12 may be translated toward and/or at least partially into the left atrium 106. At least a portion of the valve body 12 may interact with, engage, and/or be positioned adjacent to at least a portion of the mitral valve 108. For example, at least a portion of at least one cusp of the mitral valve 108 may contact at least a portion of the valve body 12. Engagement between the valve body 12 and the mitral valve 108 may restrict and/or prevent the flow of blood from the left ventricle 104 back into the left atrium 106.

In addition to the translation of the valve body 12, the mitral valve 108 may also at least partially close around the valve body 12, thereby also restricting and/or preventing the flow of blood from the left ventricle 104 to the left atrium 106. For example, as mentioned above, at least a portion of one or both of the cusps of the mitral valve may contact at least a portion of the valve body. In some embodiments, as the pressure of the blood in the left ventricle 104 increases, the pressure against the bottom 24 of the valve body 12 may increase. The increase in pressure against the bottom 24 of the valve body 12 may, in turn, increase the engagement between the valve body 12 and the mitral valve 108.

Sliding translation of the valve body 12 toward the left atrium 106 may at least partially be controlled and/or limited by the stop 28 coupled to the shaft 14. Additionally, translation of the valve body 12 toward the left atrium 106 may be at least partially limited and/or controlled by engagement between the valve body 12 and the mitral valve 108. One or both of these restrictions on the translation of the valve body 12 may, in some embodiments, prevent the valve body 12 from passing fully into the left atrium 106. Furthermore, the diameter of the enlarged portion 20 of the valve body 12 may limit and/or restrict the movement of the valve body 12 into the left atrium 106.

The preceding embodiment may, therefore, provide a mitral valve implant that is slidably translatable relative to the mitral valve to reduce and/or eliminate regurgitation. Further embodiments of a mitral valve implant having a translating valve body may be provided including various alternative valve body configurations. For example, in one embodiment a valve body may be provided generally configured as a disc including generally planar or arcuate top and bottom surfaces. In the same manner as the illustrated embodiment of FIGS. 1-3, the disc may translate along a shaft between an open position spaced from the mitral valve of the heart and closed position at least partially engaging the mitral valve and/or at least partially obstructing a flow of blood from the left ventricle to the left atrium. Implants employing a valve body having various other geometries, such as spherical, oblong, etc., may also suitably be employed. Furthermore, in addition to the slidably translatable valve body depicted in FIGS. 1-3, embodiments may be provided in which the valve body is rotatably and/or pivotally translatable to engage and/or interact with at least a portion of the mitral valve.

The illustrated mitral valve implant is shown including only a single anchor portion coupled to a proximal end of the shaft. A mitral valve implant consistent with the present disclosure may include more than one anchor portion for securing the mitral valve implant to native coronary tissue. Additional anchor portions may be employed to provide more secure coupling of the valve implant to coronary tissue. Furthermore, more than one anchor portion may be employed to achieve more precise positioning of the valve implant and/or the valve body portion of the valve implant within the heart. For example, a replacement valve may include an anchor portion coupled to the proximal end of the shaft and to the distal end of the shaft. In such an embodiment, each end of the shaft may be coupled to native coronary tissue. The orientation of the shaft, and thereby the path of translation of the valve body, may be controlled by coupling each end of the shaft to native coronary tissue. In a similar embodiment, the valve implant may include an anchor portion coupled to one end of the shaft and may include another anchor portion coupled to the shaft between the ends thereof.

A valve implant may be produced from a variety of suitable materials. Generally, such materials may be biocompatible. Suitable materials may include biocompatible polymers, such as silicone, polyurethane, etc. Various metals may additionally be used in connection with a valve implant, such as titanium, stainless steel, etc. Additionally, biological materials and/or materials which may promote cellular ingrowth may also be used in connection with a valve implant herein. Furthermore, various combinations of materials may be used herein, e.g., providing composite features and/or portions made from different materials. For example, the shaft may be formed from a metal and the valve body may be formed from a polymeric material. Various additional and/or alternative combinations may also be employed herein.

Figure 4:
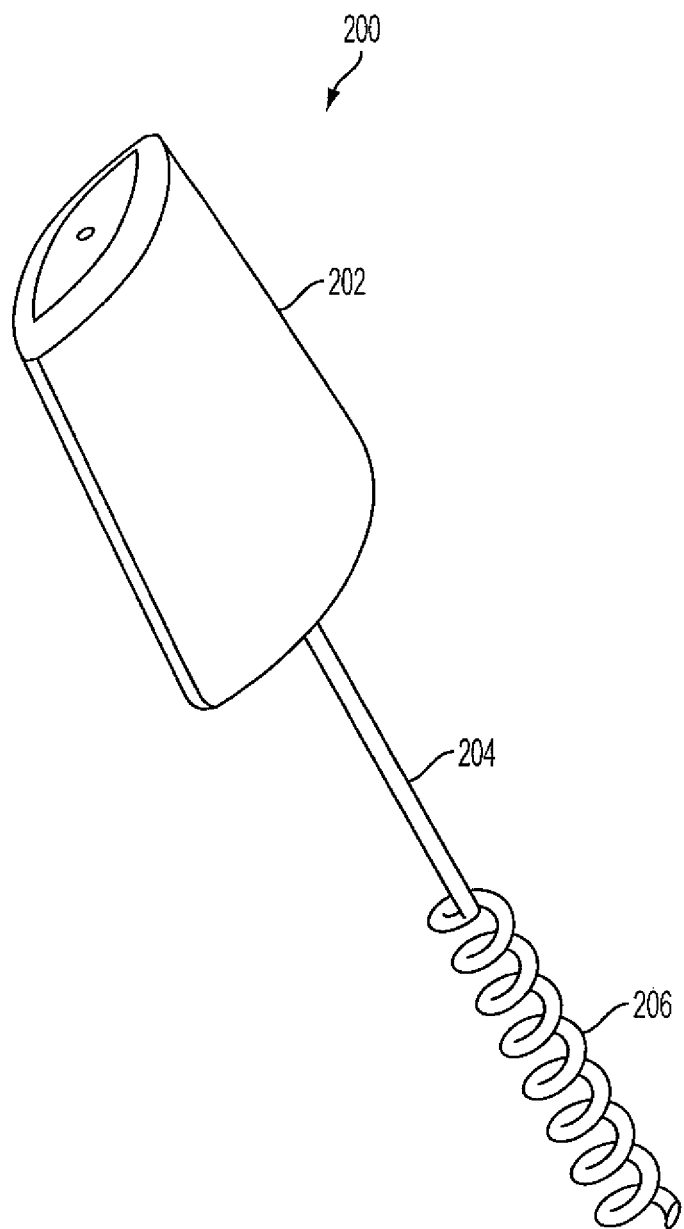
FIG. 4 depicts another embodiment of a mitral valve implant consistent with the present disclosure.

Turning to FIG. 4, another embodiment of a mitral valve implant 200 is depicted. The mitral valve implant 200 generally includes a valve body portion 202 coupled to a shaft 204. The shaft 204 may be coupled to an anchor 206. The valve body 202 may be coupled to the shaft 204 in a stationary fashion, e.g., the valve body may be coupled to the shaft in a non-slidable manner. Generally, the valve body 202 may be maintained at a generally fixed position on the shaft 204. The mitral valve implant 200 may be implanted in a heart such that the anchor 206 and the shaft 204 may maintain the valve body 202 in a position relative to various aspects of the coronary anatomy. According to one aspect, the anchor 206 and the shaft 204 may maintain the valve body 202 positioned extending at least partially within the mitral valve.

The valve body 202 may be maintained in a stationary position on the shaft 204 in various ways. For example, valve body 202 may be formed directly on the shaft 205. Additionally and/or alternatively, the valve body 202 may be adhesively bonded, welded, staked, and/or mechanically fastened to the shaft 204. Consistent with other embodiments, the shaft may include one or more stops or features which may prevent and/or limit translation of the valve body along the shaft. For example, the shaft may include a stop closely positioned on either end of the valve body, thereby restricting movement of the valve body. The stops may be fixed and/or may be adjustable along the shaft 204. Various other configurations and/or arrangements may be employed for coupling the valve body 202 in a stationary manner with respect to the shaft 204.

Similar to previous embodiments, the anchor 206 may be provided having a helical or corkscrew shape. The helical anchor 206 may be engaged with coronary tissue by rotating the anchor 206 about the axis of the helix, thereby driving the anchor 206 into native coronary tissue. Once the anchor has been engaged with native coronary tissue, the anchor 206 may resist axial pull-out from the tissue. The anchor may additionally and/or alternatively be provided having various features and/or configurations. For example, the anchor may be provided having one or more prongs which may pierce and or be embedded in coronary tissue. In one embodiment, the anchor may include a barbed prong which may resist removal of the anchor from the coronary tissue. The anchor may also be provided having suturing features. For example, the anchor may include a tab and/or ring, etc., through which a suture may pass to secure the anchor coronary tissue.

Figure 5:
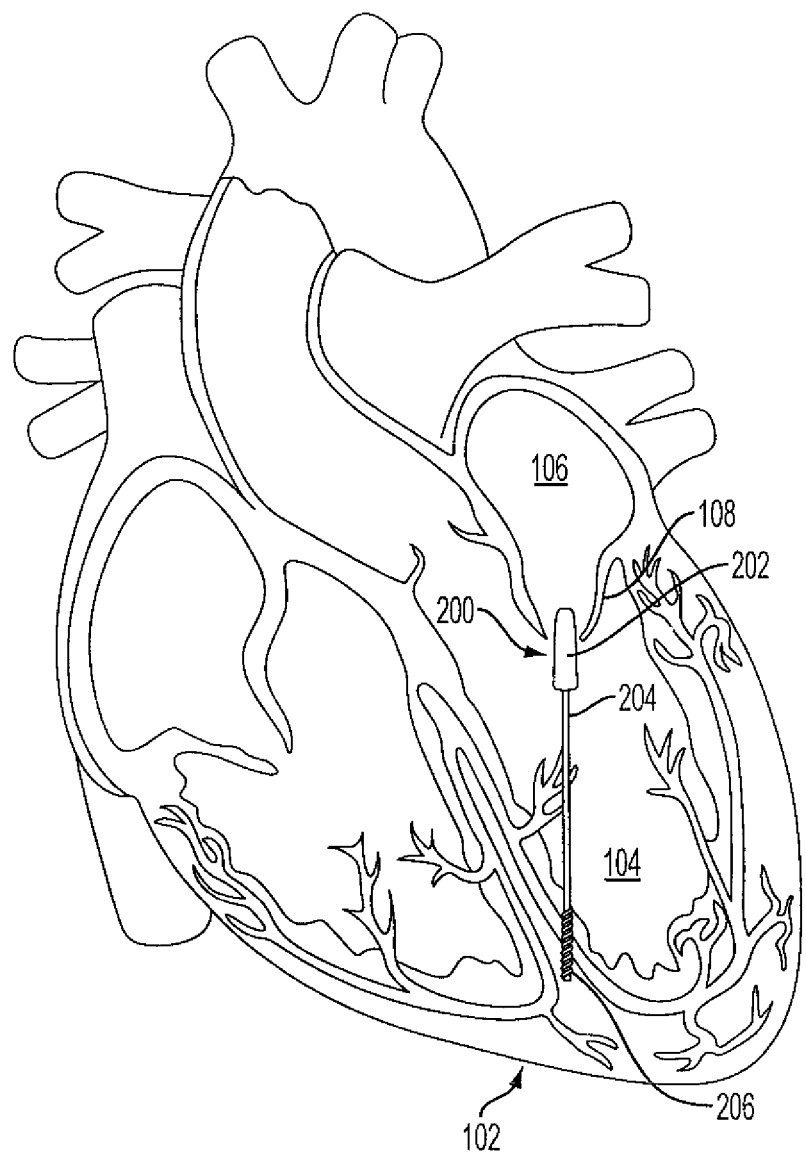
FIG. 5 depicts the mitral valve implant of FIG. 4 implanted within a heart in an open position.

Turning to FIG. 5, the mitral valve implant 200 is shown implanted within a heart 102. The mitral valve implant 200 may be positioned extending at least partially into and/or through the mitral valve 108 between the left ventricle 104 and the left atrium 106. As shown, when the pressure of blood in the left atrium 106 is higher than the pressure of blood in the left ventricle 104, for example during contraction of the left atrium 106, the mitral valve 108 may be in an open condition. In an open condition, blood may flow from the left atrium 106 through the mitral valve 108 and around the valve body 202 and into the left atrium 104.

The anchor 206 may be engaged in native coronary tissue surrounding and/or defining at least a portion of the left ventricle 104. The valve body 202 may be positioned extending at least partially into and/or through the mitral valve 108 by the shaft 204 extending between the anchor 206 and the valve body 202. In a related embodiment, the anchor may be engaged in tissue surrounding and/or defining at least a portion of the left atrium. Similar to the preceding embodiment, the valve body 202 may be positioned extending at least partially into and/or through the mitral valve 108 by the shaft 204 extending between the anchor 206 and the valve body 202.

Consistent with a further embodiment, the mitral valve implant may include more than one anchor for positioning the valve body relative to the mitral valve. For example, the shaft may include an anchor coupled to each end of the shaft. The shaft may be provided extending through the mitral valve, with one anchor being engaged with coronary tissue on the ventricle side of the mitral valve. The other anchor may be engaged with coronary tissue on the atrium side of the mitral valve. As with the previous embodiments, the valve body may be coupled in a stationary position on the shaft, such that the valve body is positioned extending at least partially into and/or at least partially through the mitral valve.

Figure 6:
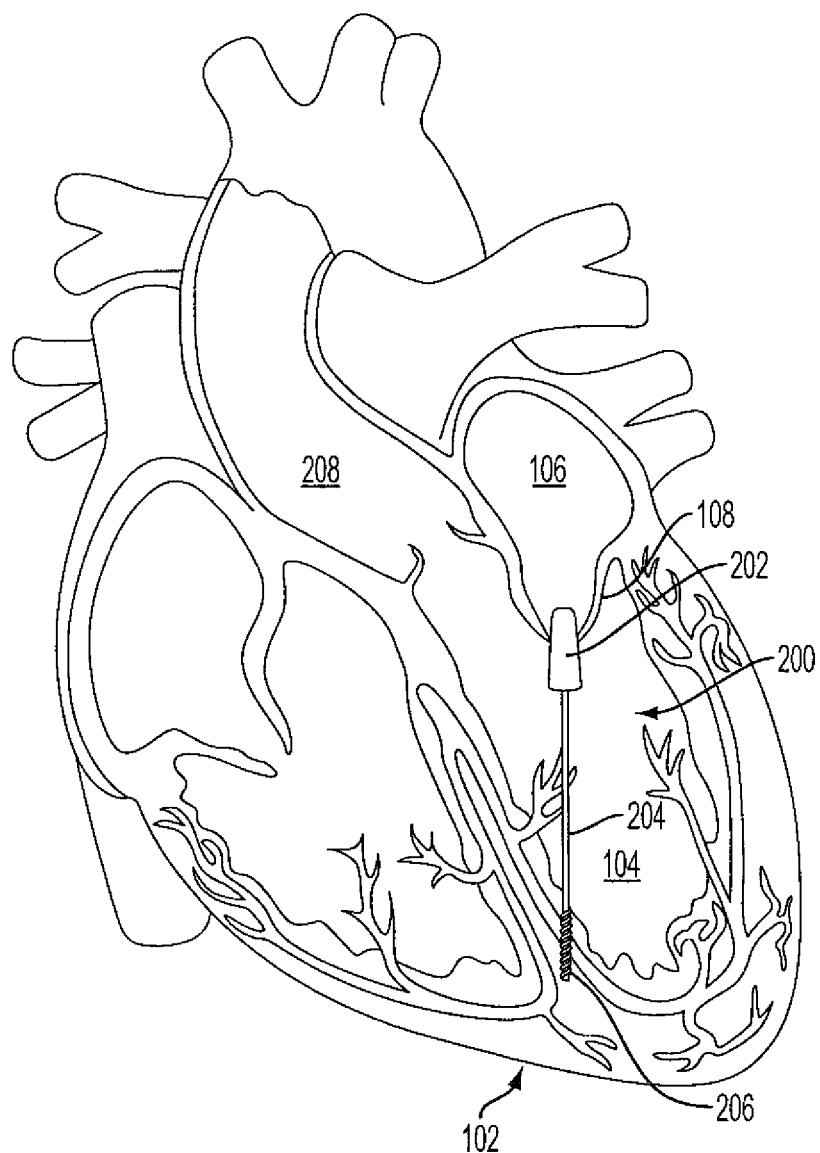
FIG. 6 depicts the mitral valve implant of FIG. 4 implanted within a heart in a closed position.

FIG. 6 depicts the mitral valve implant 200 implanted in a heart 102 with the mitral valve 108 in a closed condition. The closed condition of the mitral valve 108 may occur when the pressure of blood in the left ventricle 104 is higher than the pressure of blood in the left atrium 106. As shown, when the mitral valve 108 is in a closed condition at least a portion of the mitral valve 108 may interact with, engage, and/or seal against the valve body 202 of the mitral valve implant 200. The presence of the mitral valve implant 200 may reduce the amount of closure of the mitral valve 108 that is necessary to achieve an adequate seal to permit ejection of blood from the ventricle 104 through the aorta 208, i.e., to prevent and/or reduce mitral regurgitation.

The valve body 202 may be shaped to facilitate the flow of blood from the left atrium 106 to the left ventricle 104 when the mitral valve 108 is open. The valve body 202 may have a generally streamlined shape, allowing the smooth flow of blood around the valve body 202. Other embodiments of the mitral valve implant may provide less consideration for the flow characteristics of blood flowing around the valve body. The valve body may have a generally cylindrical, prismatic, etc. shape, without limitation.

The performance of the mitral valve implant 200 for reducing and/or eliminating mitral valve regurgitation may be, at least in part, related to the positioning of valve body 202 relative to the mitral valve 108. In an embodiment consistent with this aspect, during implantation of the mitral valve implant, the valve body 202 may be slidably positionable along the shaft 204. Once the anchor 206 is engaged with native coronary tissue the valve body 202 may be translated along the shaft 204 and may be positioned relative to the mitral valve 108, e.g., such that the valve body 202 extends at least partially within the mitral valve 108. Slidable positioning of the valve body 202 along the shaft 204 after the mitral valve implant 200 has been delivered to the heart 102 may allow the performance of the mitral valve implant 200 to be adjusted. Furthermore, the adjustability of the position of the valve body 202 may accommodate any errors in the position of the anchor 206 in the heart 102, and/or may render the successful implantation of the mitral valve implant 200 less dependent upon accurate placement of the anchor 206. Once the valve body 202 has been positioned, the position of the valve body 202 on the shaft 204 may be fixed, e.g. by frictional engagement between the valve body 202 and the shaft 204, etc.

The illustrated and described embodiments of the mitral valve implant have utilized an implant body coupled to a shaft. The shaft, as used herein, may be a rigid, semi-rigid. In further embodiments, the shaft may be a flexible member. Consistent with such embodiments, the shaft may be a flexible wire or filament, etc. In some embodiments, the flexible wire or filament may be coupled to at least two anchor portions. For example, the flexible wire or filament may extend through the valve body. An anchor may be coupled to the flexible wire or filament on each side of the valve body. For example, the flexible wire or filament may position the valve body relative to the mitral valve and may be coupled to the left ventricle and to the left atrium, on either side of the valve body.

An embodiment of a mitral valve implant including a flexible wire and/or filament may suitably be employed in embodiments including a translating valve body, in which the valve body may slidably translate along the flexible wire or filament. In a related embodiment, the valve body may be non-slidably coupled to the flexible wire or filament. The flexible wire or filament may be provided having a length which may permit the valve body to move toward and away from the mitral valve utilizing the flexibility of the flexible wire or filament.

Furthermore, an embodiment of a mitral valve implant including a flexible wire or filament may also suitably be employed in an embodiment including a generally stationary implant body. According to such an embodiment, the implant body may be generally non-slidably coupled to the flexible wire or filament. The flexible wire or filament may be coupled to native coronary tissue, e.g., via anchor portions, etc., on either side of the valve body. Coupling the flexible wire or filament on either side of the valve body may generally maintain the valve body in a position within and/or relative to the mitral valve.

Figure 7:
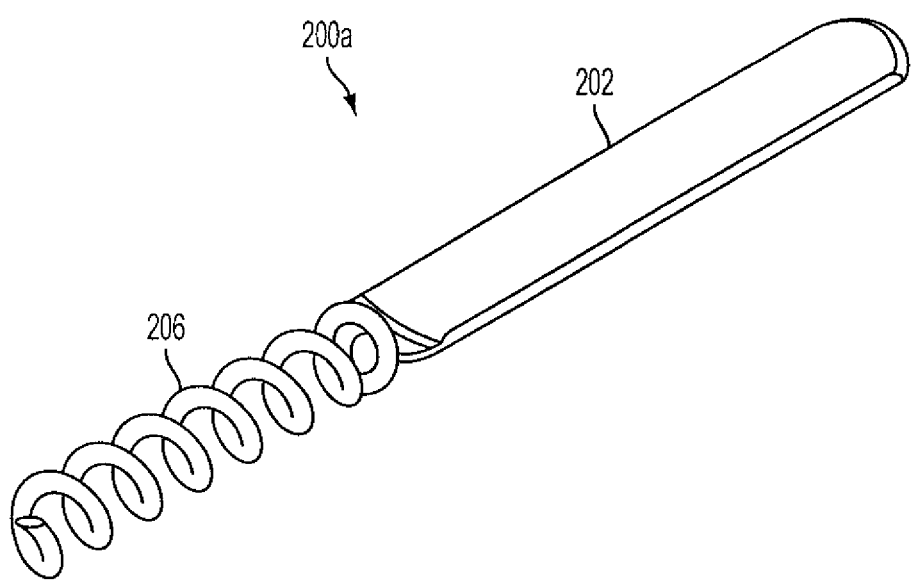
FIG. 7 shows another embodiment of a mitral valve implant consistent with the present disclosure.

Turning to FIG. 7, another embodiment of a mitral valve implant 200a is shown. Similar to the previously described embodiment, the mitral valve implant 200a may generally include a valve body 202 configured to reduce and/or eliminate mitral valve regurgitation. In contrast to the preceding embodiment, an anchor 206 may be coupled to the valve body 202. As shown, the anchor 206 may be directly coupled to the valve body 202 without a shaft extending between the anchor 206 and the valve body 202.

As mentioned above, various different features and/or arrangements may be used for attaching and/or securing the mitral valve implant relative to coronary anatomy. FIG. 8 depicts another embodiment of a mitral valve implant 200b according to the present disclosure including an alternative anchor 206a. As shown, the mitral valve implant 200b may include a valve body 202 coupled directly to the anchor 206a. Alternatively, the valve body may be indirectly coupled to the anchor, e.g., by a shaft. The anchor 206a may generally include one or more prongs, stems, etc. 205. The prong 205 may include one or more barbs 207. The mitral valve implant 200b may be attached and/or secured to native coronary tissue by piercing the anchor 206a at least partially into native coronary tissue. The one or more barbs 207 may engage the coronary tissue and resist removal of the anchor 206a from the coronary tissue.

In a related embodiment, an anchor including one or more barbs may be employed in connection with a translating mitral valve implant configuration, as shown and described herein. In such and embodiment, the valve body may be translatable relative to the native mitral valve. For example, the valve body may be coupled to the anchor by a shaft extending therebetween. The valve body may be slidable along the shaft, permitting the valve body the translate relative to the mitral valve. Various alternative and/or additional related embodiments may also be provided consistent with this aspect of the present disclosure.

Figure 9:
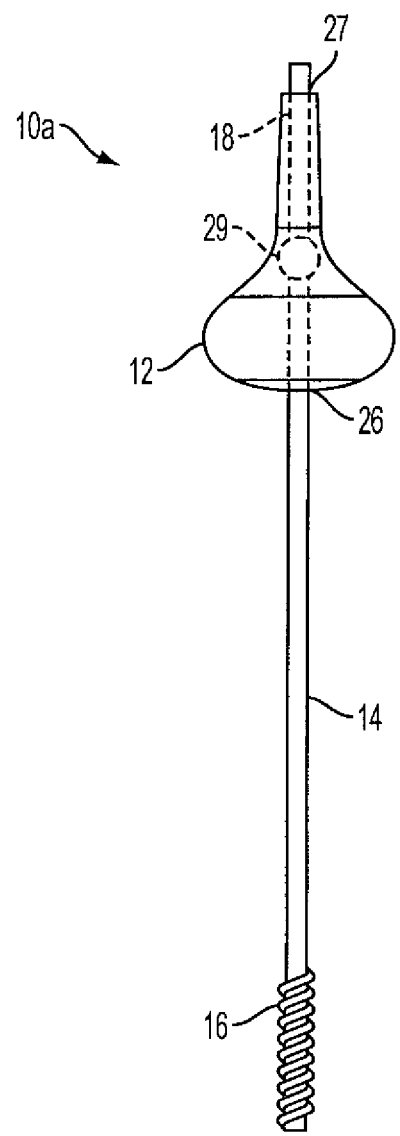
FIG. 9 depicts another embodiment of a translating mitral valve implant consistent with the present disclosure.
Figure 9:
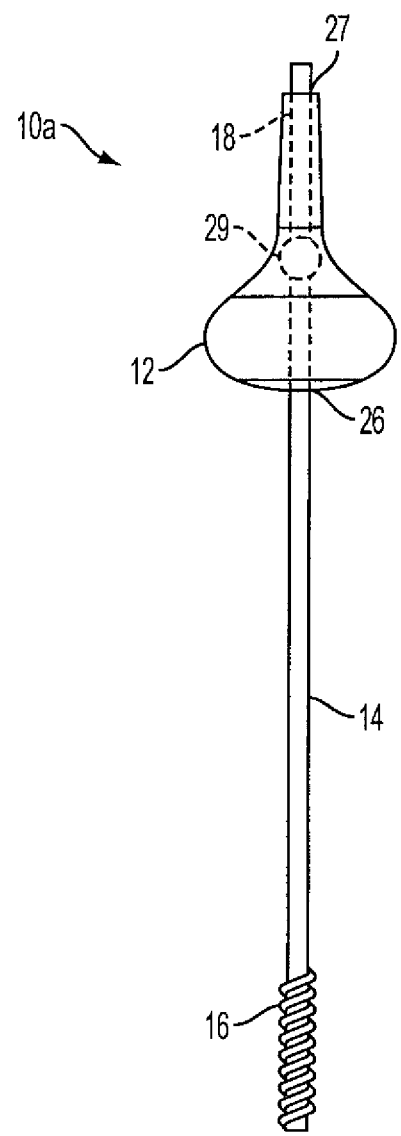

Turning to FIG. 9, another embodiment of a movable and/or translatable mitral valve implant 10a is depicted. Similar to the previously described embodiment, the mitral valve implant 10 may generally include a valve body 12 slidably coupled to a shaft 14. The mitral valve 10a may further include an anchor 16 coupled to the shaft 14 and configured to secure and/or attach the mitral valve implant 10a to native coronary tissue. As shown in broken line, the mitral valve implant 10a may include a single stop 29 configured to restrict and/or control the range of movement of the valve body 12 along the shaft 14. As shown, the stop 29 may be disposed at least partially within the valve body 12 and the range of movement of the valve body 12 may be restricted by an interaction between the stop 29 and an inner wall and/or portion of the valve body 12.

As shown, the shaft 14 may extend at least partially though the valve body 12, e.g., through respective openings 26 and 27 at opposed ends of the valve body 12. The stop 29 may be an enlarged region of the shaft 14, and/or a bead or other member disposed on the shaft 14. The stop 29 may be dimensioned to prevent and/or restrict passage of the stop 29 through one or both of the openings 26, 27 in the valve body 12. The valve body 12 may, therefore, translate along the shaft 14 with the range of movement being controlled and/or restricted by the interaction of the stop 29 and the openings 26, 27 and/or with an interior wall of the valve body 12.

According to one embodiment of a mitral valve implant 10a including a single stop 29 for controlling the range of movement of the valve body 12, the stop 29 may be installed inside of the valve body by elastically deforming one of the openings 26, 27 over the stop 29. One of the openings 26, 27 may be elastically deformed by pushing the stop against the opening 26, 27 causing the valve body 12 to deform and the opening 26, 27 to expand to permit entrance of the stop 29 into the valve body 12. The valve body 12 may subsequently at least partially elastically recover to resist subsequent removal of the stop 29 from the valve body 12. Deformation and/or elastic recovery of the valve body 12 may be aided by heating the valve body and/or the stop. In a related embodiment, the stop may also and/or alternatively elastically deform to permit assembly of the mitral valve implant. Various additional and/or alternative methods may also be employed for forming a mitral valve implant including a single stop for restricting and/or controlling the range of movement of the valve body.

A mitral valve implant according to the present disclosure may be implanted using a variety of surgical an/or non-surgical procedures and/or minimally invasive surgical procedures. A surgical implantation procedure may include, for example, an open heart procedure in which the implant may be directly placed into the heart and manually positioned relative to the mitral valve.

A mitral valve implant consistent with the present disclosure may also advantageously be implanted using less invasive procedures. For example, the mitral valve implant may be implanted using a percutaneous procedure. A suitable percutaneous implantation procedure may include a catheterization procedure. Generally, in a percutaneous catheterization procedure the mitral valve implant may be delivered to the heart using a catheter inserted into a vein or artery, depending upon the desired delivery sight, and into the left atrium or the left ventricle. In one such embodiment, the mitral valve implant may be delivered via a transceptal approach, in which the catheter is inserted, e.g., via a vein, into the right atrium. The catheter may then pass through a puncture between the right atrium to the left atrium and further through the mitral valve to the left ventricle, if desired. Generally, according to a catheterization procedure, the vein or artery may be accessed through a percutaneous incision or puncture. A catheter carrying the mitral valve implant may be introduced into the vein or artery through the incision or puncture. The catheter and mitral valve implant may be passed through the vein or artery into the heart. Once in the heart, the mitral valve implant may be deployed from the catheter and positioned within and/or between the left ventricle and the left atrium.

Figure 10:
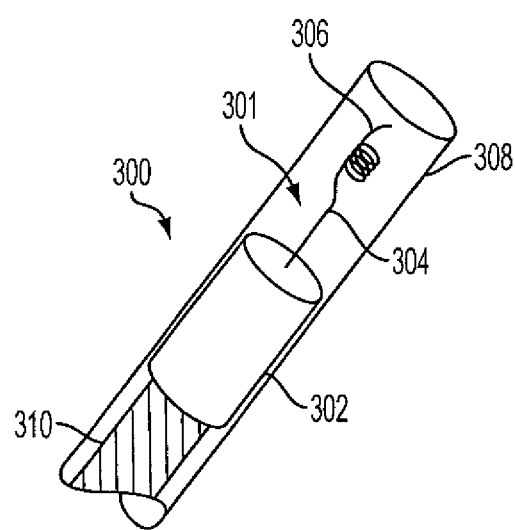
FIG. 10 schematically shows and embodiment of a percutaneous mitral valve implant delivery system consistent with the present disclosure.

Turning next to FIG. 10, an embodiment of a percutaneous delivery system 300 for a mitral valve implant 301 is shown. As previously described, the mitral valve implant 301 may generally include a valve body 302 and an anchor 306. According to some embodiments, the mitral valve 301 may further include a shaft 304 which is coupled between the valve body 302 and the anchor 306. As depicted, the mitral valve implant 301 may be loaded into a catheter 308. According to a further embodiment, the mitral valve implant may be carried by a conveyance feature, such as an enlarged region of a catheter and/or a chamber or pod couple to the catheter.

As generally outlined above, with the mitral valve implant 301 loaded in the catheter 308 and/or within a conveyance feature associated with the catheter, at least a portion of the catheter 308 may be inserted into a vein or artery and passed through the vessels, i.e., veins and/or arteries, to the heart. Conveyance of the catheter 308 and/or of the mitral valve implant 301 to the heart may be directed and/or assisted by monitoring the travel of the catheter 308, e.g., via radiographic and/or other imaging techniques, etc. For example, at least a portion of the catheter 308 and/or at least a portion of the mitral valve implant 301 may include a radio-opaque material, allowing the position of the catheter 308 and/or of the mitral valve implant 301 to be radiographically monitored or determined.

Once the mitral valve implant 301 has been delivered to the heart, the mitral valve implant 301 may be implanted by positioning and securing the implant 301 within the heart and deploying the implant 301 from the catheter 308. The implant 301 may be secured within the heart by engaging the anchor 306 with native coronary tissue. Utilizing a helical anchor 306, as shown, the mitral valve implant 301 may be secured by pressing the anchor 306 into coronary tissue and rotationally advancing the anchor 306 into coronary tissue. Rotationally advancing the anchor 306 may be achieved by rotating the entire catheter 308, and or at least a portion of the catheter 308, and thereby also rotating the anchor 306 relative to the coronary tissue. Alternatively, the anchor and/or the entire mitral valve implant may be rotated independently of the catheter, e.g., by a drive lead, such as a flexible drive shaft, extending through at least a portion of the catheter and coupled to the mitral valve implant and/or coupled to the anchor. According to various other embodiments, the anchor of the mitral valve implant may include suturing features, barbs and/or prongs, etc. Suitable corresponding operations may be employed for engaging such anchor features with native coronary tissue.

The mitral valve implant 301 may be deployed from the catheter 308, or other conveyance feature by pushing the mitral valve implant 301 from the catheter. For example, a pushrod 310, etc., may extend through at least a portion of the catheter 308. The pushrod 310 may be axially advanced through the catheter 308 to force the mitral valve implant 301 from the lumen of the catheter 308. In a related embodiment, the mitral valve implant may be deployed from the catheter via hydraulic force. For example, a fluid may be forced through the catheter. The fluid may bear on, and may hydraulically eject the mitral valve implant from the catheter. In still a further embodiment, the mitral valve implant may be pulled from the catheter. The anchor may be engaged with coronary tissue, and the catheter may be withdrawn from the anchor site, leaving the mitral valve implant engaged with the coronary tissue. Combinations of the foregoing deployment techniques, as well as other known deployment techniques, may also suitable be employed.

The mitral valve implant 301 may be positioned relative to the coronary anatomy before, during or after deployment of the mitral valve implant 301 from the catheter 308. For example, the anchor portion 306 of the mitral valve implant 301 may be engaged with coronary tissue. The valve body 302 and shaft 304 may then be positioned relative to coronary anatomy by manipulation of the catheter 308, etc. Once the mitral valve implant 301 has been arranged relative to coronary anatomy, the mitral valve implant 301 may be fully deployed from the catheter 308. Alternatively, the mitral valve implant 301 may be fully deployed from the catheter 308. Following deployment, the mitral valve implant 301 may be manipulated to achieve a position and/or arrangement relative to coronary anatomy. Consistent with such an embodiment, the anchor 306 of the mitral valve implant 301 may be engaged with coronary tissue before, during, or after complete deployment of the mitral valve implant 301. Various other techniques and methods may also suitably be employed.

At least a portion of the mitral valve implant 301 may be collapsible and/or reducible in volume to facilitate percutaneous and/or transluminal delivery. In such a manner, the valve body 302 of the mitral valve implant 301 may be a collapsible member, which can be reduced in volume and/or reduced in maximum diameter during delivery to the heart and/or during placement and/or attachment of the anchor to native coronary tissue. After delivery to the heart, the valve body 302 may be expanded, inflated, and/or otherwise increased in volume or size. Accordingly, the mitral valve implant 301 may be delivered to an implantation site via a smaller diameter catheter, and/or via smaller vessels, than would otherwise be required.

Figure 11:
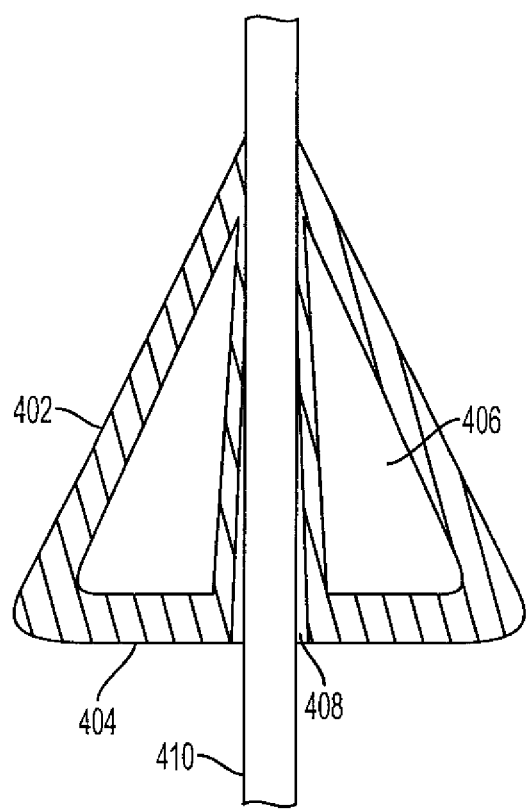
FIG. 11 is a cross-sectional view of an embodiment of an inflatable valve body consistent with the present disclosure.

With reference to FIG. 11, according to one embodiment, the mitral valve implant may include an inflatable valve body 402. An inflatable valve body 402 may include an at least partially deformable body 404 defining at least one cavity 406. The body 404 may further define an opening 408 capable of receiving at least a portion of a shaft 410 therein. Additionally or alternatively, the body may include one or more features for coupling the body to a shaft.

The at least partially deformable valve body 404 may be collapsed to a reduced size, which may, for example, allow the valve body 404 to be loaded into a catheter delivery system. Such a catheter delivery system may be suitable for transluminal delivery of a mitral valve implant, including the inflatable valve body 402, to the heart. In addition to being collapsed, the valve body 402 may be deformed to facilitate loading into a catheter delivery system. For example, the valve body 402 may be collapsed and may be rolled and/or folded to a generally cylindrical shape, allowing the valve body 402 to be loaded in a catheter having a circular lumen.

A collapsed and/or rolled or folded valve body 402 may be inflated, restoring the valve body 402 to expanded configuration. For example, a collapsed and/or rolled or folded valve body 402 may be inflated and restored to an expanded configuration once the mitral valve implant has been delivered to the heart and deployed from a catheter delivery system. Inflating the valve body 402 may be carried out by introducing a fluid, such as saline, into the at least one cavity 406. In addition to a liquid, such as saline, the valve body may be inflated with a setting or curable fluid. The setting or curable fluid may set and/or be cured to a solid and/or semi-solid state within the cavity of the valve body. An example of such a material may be a thermoset polymer resin, a gel material, such as silicone gel, etc.

According to one embodiment, after delivery to the heart and deployment from the catheter delivery system, the at least one cavity may be filled with a fluid by injecting the fluid into the cavity via a filling tube extending through and/or with the catheter delivery system. Other filling methods and systems may also suitably be employed herein. In an inflated state, the valve body may be shaped and/or configured for use in connection with a translating and/or a stationary mitral valve implant, as described previously.

Figure 12:
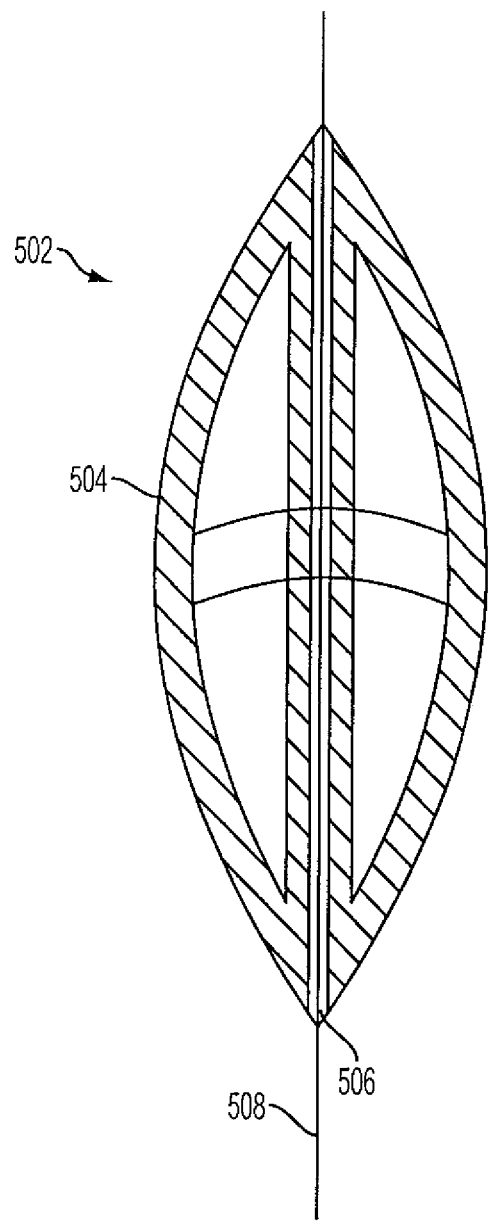
FIG. 12 is a cross-sectional view of an embodiment of an expandable valve body consistent with the present disclosure.

According to another embodiment, shown in FIG. 12, the valve body 502 may be expandable. An embodiment of an expandable valve body 502 suitable for use in connection with a mitral valve implant herein may include a recoverably deformable shell 504 defining the shape of the valve body 502. Similar to previous embodiments, the valve body 502 may include an opening 506 for receiving a shaft 508 of a mitral valve implant at least partially therein. According to one embodiment, the opening 506 may provide a passage extending through the valve body 502. Additionally and/or alternatively, the valve body may include features for coupling the valve body to the shaft.

The recoverably deformable shell 504 may be deformable, for example, to permit the valve body 502 to be collapsed, folded, rolled, etc., for loading into a catheter delivery system, and/or to facilitate delivery of a mitral valve implant including the valve body 502 to an implantation site, e.g., within the heart. The recoverably deformable shell 504 may further be recoverable, allowing the valve body 502 to return to the expanded configuration from a deformed configuration.

Consistent with one aspect, the deformable shell 504 may include a resiliently deformable material, such as an elastomer, which may be elastically deformed under stress. The deformable shell 504 may elastically recover when the stress is removed. In such an embodiment, the deformable shell 504 may, for example, be deformed from an expanded configuration to a collapsed condition and loaded into a catheter delivery system. After delivery to an implant site, the deformable shell 504 may be deployed from the catheter delivery system, thereby removing the deforming stress from the valve body 502. Once the deforming stress is removed, the deformable shell 504 may resiliently recover back to the expanded configuration.

In a related embodiment, the deformable shell may include a shape memory material, such as Nitinol, etc. The deformable shell may be collapsed and/or deformed to facilitate delivery of the implant to the desired site, e.g., via a transluminal and/or a surgical procedure. The deformable shell may subsequently be recovered to an expanded configuration. In an embodiment using a thermally activated shape memory material, recovery of the shape memory deformable shell may be accomplished by heating the deformable shell to, or above, an activation temperature. Heat for activating the shape memory material may be provided by the body temperature of the subject receiving the mitral valve implant, and/or from an external source, e.g., via the catheter, etc.

An embodiment of mitral valve implant may include an expandable/recoverable valve body including a cellular material. The cellular material may be, for example, a deformable and/or compressible expanded material, such as a polymeric foam material. The valve body may be deformed, compressed, and/or collapsed to a reduced volume configuration, at least in part, by compressing or deforming the cellular material. The mitral valve implant may be transported to an implant site as disclosed. When the implant is deployed from the delivery system the valve body may recover to a generally original volume and/or configuration. Recovery of the valve body may include recovery and/or expansion of the cellular material.

Figure 13:
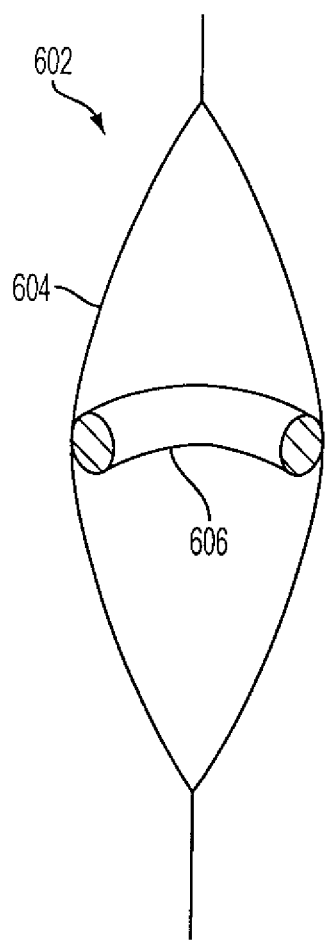
FIG. 13 is a cross-sectional view of an embodiment of an expandable valve body consistent with the present disclosure including a recoverably deformable rib.

In another related embodiment, depicted in FIG. 13, an expandable valve body 602 may include deformable and/or flexible outer shell 604. The outer shell 604 may be supported in an expanded configuration by one or more recoverably deformable supports. In the embodiment of FIG. 13, the recoverably deformable support may be provided as a resiliently deformable rib 606. The deformable shell 604 may be a resiliently deformable material and/or may be a flexible material. The resiliently deformable rib 606 and/or the deformable shell 604 may be deformed, e.g., to collapse the valve body 602 from an expanded configuration, under a deforming stress. As discussed with reference to other embodiments, collapsing the valve body 602 may facilitate transport to an mitral valve implant, for example, using a catheter delivery system. When the deforming stress is released, e.g., by deploying the valve body 602 from a delivery system, the recoverably deformable rib 606 and/or the deformable outer shell 604 may resiliently recover to restore the valve body 602 to an expanded condition. While only a single rib is depicted in the illustrated embodiment, the valve body may alternatively include a plurality of recoverably deformable ribs.

Figure 14:
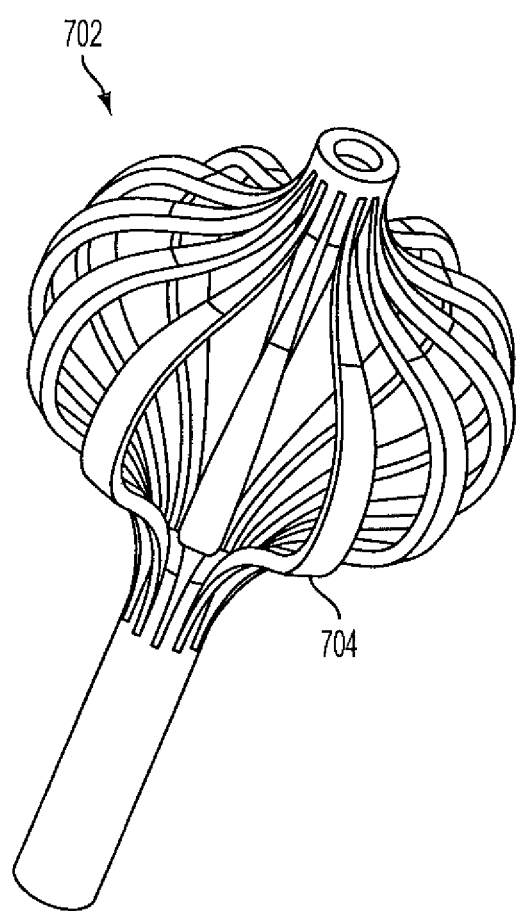
FIG. 14 is a cross-sectional view of another embodiment of an expandable valve body consistent with the present disclosure including recoverably deformable stringers.

In various embodiments, the recoverably deformable supports may be configured as ribs, generally having a transverse orientation relative to the axis of the valve body, such as depicted in FIG. 13. In additional and/or alternative embodiments, a valve body 702 may include a deformable and/or flexible outer shell (not shown) covering and/or supported by recoverably deformable supports in the form of resiliently deformable stringers 704. As depicted in FIG. 14, the recoverably deformable stringers 704 may be generally oriented along the longitudinal axis of the valve body 702. In a further embodiment, the recoverably deformable supports may be configured as a lattice, scaffolding, etc. supporting a deformable and/or flexible outer shell of the valve body. Further embodiments may include combinations ribs and stringers. Various other configurations of recoverably deformable supports may also suitably be employed.

In addition to resiliently recoverable shell, supports, etc., a mitral valve implant may include a valve body having an outer shell and/or having supports which may be controllably recoverable. For example, an outer shell and/or one or more supports of a mitral valve implant valve body may be formed from a shape memory material. Such materials may include shape memory metal alloys, shape memory polymers, etc. Consistent with such embodiments, the valve body may be collapsed and/or otherwise deformed from an expanded configuration. The collapsed and/or deformed valve body may maintain the collapsed and/or deformed configuration after the initial deforming stress is released. The valve body may subsequently be returned to the expanded and/or operable configuration, for example, by heating the valve body above an activation temperature of the shape memory material, which may induce recovery of the shape memory material to a pre-deformed shape. The activation temperature inducing recovery of the deformed valve body may be provided by the body temperature of the patient receiving the mitral valve implant. Alternatively, heat for activating recovery of the shape memory material may be provided by a heating element coupled to the valve body and/or a heating element delivered through a catheter. In other embodiments, activating heat may be provided by irradiating the shape memory material, e.g., with microwaves, IR light, etc.

Figure 15:
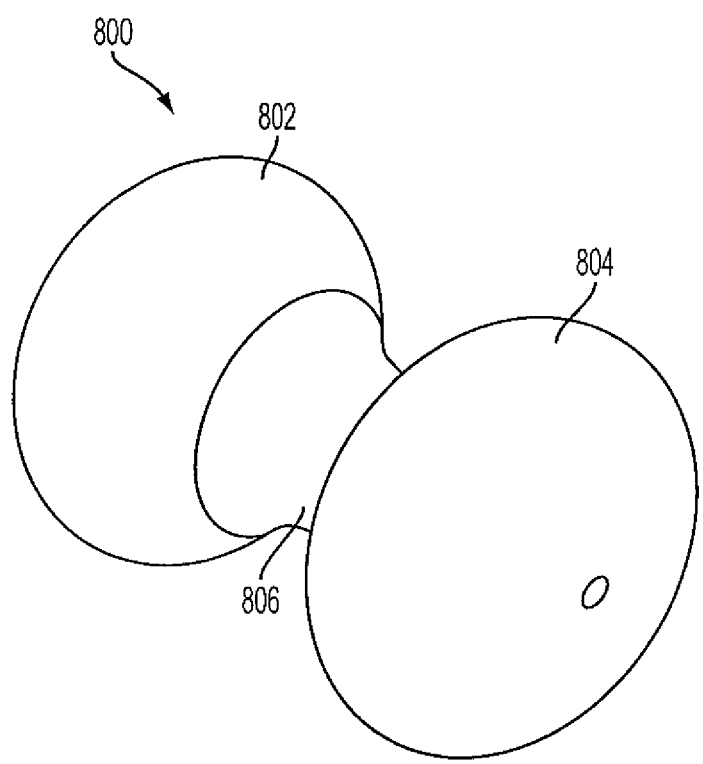
FIG. 15 is perspective view of a valve body of yet another embodiment of a mitral valve implant consistent with the present disclosure.

Another embodiment of a valve body 800, suitable for use in a mitral valve implant, is shown in FIG. 15. The valve body 800 may include first and second enlarged portions 802, 804 joined by a narrow region 806. In one such embodiment, the valve body may have a generally hourglass shape, as shown. The valve body 800 may be positioned relative to a mitral valve such that the first enlarged portion 802 may be disposed at least partially within the left atrium and the second enlarged portion may be disposed at least partially within the left ventricle. The valve body may be maintained in position relative to the coronary anatomy by an anchor and/or a shaft consistent with any preceding embodiment. Additionally, the valve body 800 may be a collapsible and/or expandable member consistent with any previously discussed embodiment.

Figure 16A:
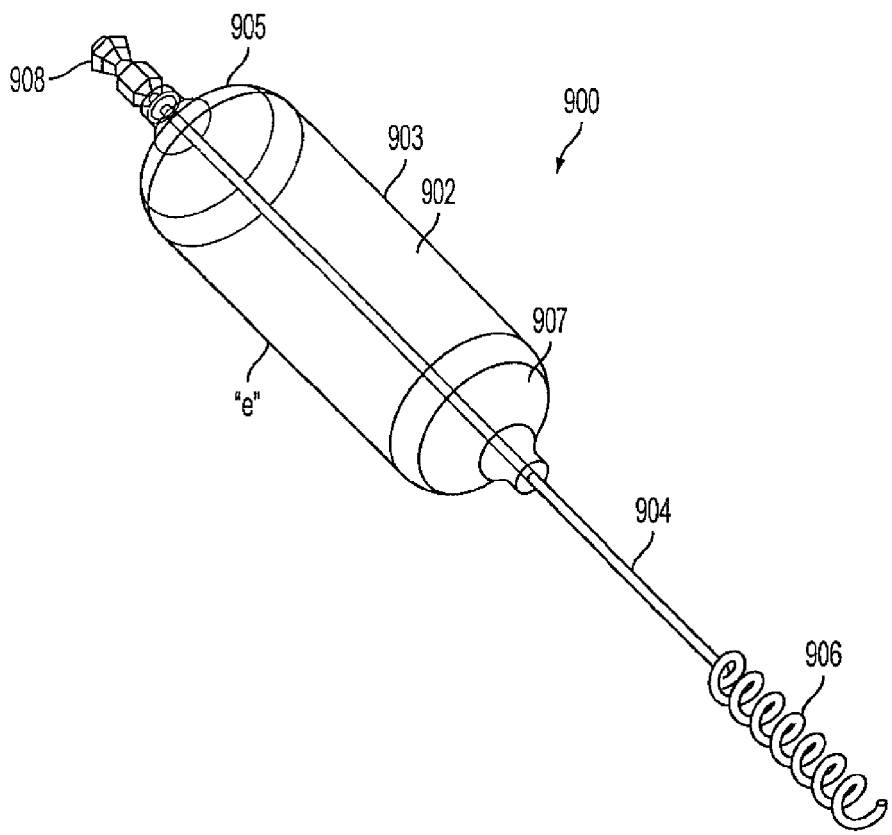
FIG. 16A is a perspective view of an additional embodiment of a mitral valve implant in accordance with the present disclosure.
Figure 16B:
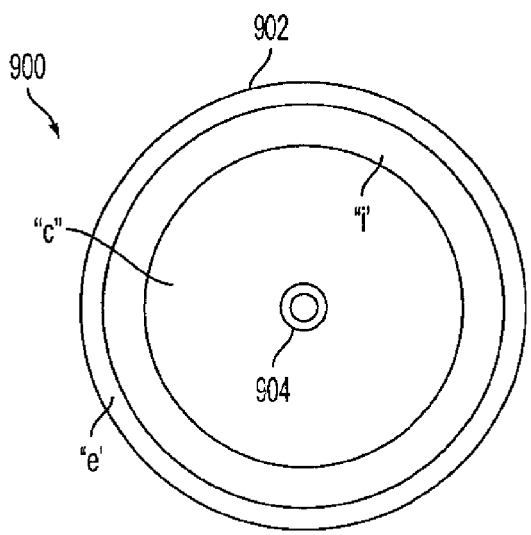
FIG. 16B is a cross-sectional view of the mitral valve implant shown in FIG. 16A.

Referring now to FIGS. 16A-16B, another embodiment of a mitral valve implant 900 is shown. Mitral valve implant 900 generally includes expandable member 902, shaft 904 and anchor 906. Expandable member 902 may be an inflatable member capable of expanding or contracting in order to conform with portions of the mitral valve. For example, expandable member 902 may expand until the exterior surface "e" of expandable member 902 approaches or conforms with one or more of the leaflets and/or cusps of the mitral valve.

Expandable member 902 may include a central portion 903, proximal end 905 and distal end 907. Ends 905, 907 of expandable member 902 may each be tapered and configured to form an opening capable of allowing shaft 904 to pass therethrough. This opening could be configured into a variety of different geometries including, but not limited to, circular, square, oval, etc. Ends 905, 907 may be configured to form a seal around shaft 904 in order to prevent the inflation medium from escaping before, during or after inflation. In some embodiments, proximal end 905 may be connected to a connecting member 908, which may include a valve portion (not shown) for insufflation/deflation. Proximal and distal ends 905, 907 may be expandable, however, in other embodiments proximal and distal ends 905, 907 may be constructed out of a rigid non-expandable material, leaving an expandable central portion 903.

Expandable member 902 may include central portion 903 as well as proximal and distal ends 905, 907. Central portion 903 may be monolithically formed with proximal and distal ends 905 and 907. Alternatively, central portion 903 may be configured to connect with proximal and distal ends 905 and 907 to form a seal. Expandable member 902 may be constructed out of a variety of different materials. Some expanding materials may include polymeric materials, elastomeric materials, rubber, latex, chloroprene, nylon fabrics, or any other suitable materials. The exterior surface "e" of expandable member 902 may be smooth or rough and may include ridges or irregular contours capable of receiving portions of the mitral valve. In some embodiments, the exterior surface of expandable member 902 may include a fabric material capable of contacting and interacting with the leaflets of the mitral valve. In some embodiments, central portion 903 may also include a coating, which may provide a non-stick surface. Central portion 903 may include other materials as well including, but not limited to, fabric materials, microfibers, nanomaterials, etc. Ends 905 and 907 may include similar materials.

In some embodiments, shaft 904 may be securely attached to the proximal and/or distal ends 905, 907 of expandable member 902. This attachment may be achieved using welding or any other suitable connection. Shaft 904 may also include anchor portion 906, which may be constructed in a variety of different configurations such as the helical arrangement described hereinabove. In some embodiments, expandable member 902 may be slidably movable about shaft 904. For example, expandable member 902 may slide about shaft 904 in a distal direction until reaching anchor portion 906. Similarly, expandable member 902 may be configured to slide in a proximal direction before coming into contact with connecting member 908. Stops, such as those described herein, may be employed to limit the axial movement of expandable member 902. In some embodiments, expandable member 902 may be adjusted and placed in different positions along shaft 904. For example, shaft 904 may include ridges or other adjustment mechanisms capable of forming an interface with ends 905 and 907 of expandable member 902. Using this type of arrangement, expandable member 902 may be adjusted to a number of different positions along shaft 904. Shaft 904 may be constructed out of a variety of different materials and may be rigid or flexible in nature. Moreover, shaft 904 may be hollow and may further include a variety of apertures capable of transporting an inflation medium to the interior "i" of expandable member 902. In some embodiments, the hollow shaft may receive an inflation medium from a hose affixed to connecting member 908. Upon entering the hollow shaft this medium may travel in a distal direction until reaching the plurality of apertures, at which point the medium may exit shaft 904 and insufflate the interior of expandable member 902. Shaft 904 may be entirely solid or entirely hollow or may include both solid and hollow portions. For example, shaft 904 may be hollow until the distal end 907 of expandable member 902 is reached and solid thereafter.

Connecting member 908 may establish a connection between expandable member 902 and a conduit (not shown) such as a hose or other device. This conduit may be connected to an inflation device in order to provide the necessary expansion to expandable member 902. Expandable member 902 may include pressure sensors and may be capable of indicating the current pressure within the interior of expandable member 902. This information may be provided to the inflation device using telemetry or any other suitable techniques.

Expandable member 902 may be configured to receive a variety of different substances through connecting member 908. These substances may include, but are not limited to, liquids, gases (e.g., air, helium, hydrogen, nitrous oxide), gels, flouro visible materials, etc. Connecting member 908 may be affixed to the conduit and/or expandable member 902 using a variety of different arrangements, including but not limited to, compression fittings, ferrules, screw-fittings, snap-fittings, press-fittings, welding, threaded rod, etc. In some embodiments connecting member 908 may be monolithically formed with expandable member 902 and/or shaft 904. Connecting member may further include a valve portion (not shown) that may be used to inflate or deflate expandable member 902. Valve portion (not shown) may include but is not limited to, ball-check valves, swing-check valves, clapper valves, stop-check valves and lift-check valves.

Expandable member 902 may be detachably removable from shaft 904 using a variety of different techniques, including, but not limited to, by disconnecting connecting member 908 from shaft 904 and/or expandable member 902. For example, if expandable member 902 is defective or in need of replacement, connecting member 908 may be disconnected and expandable member 902 may be removed and a new valve body may be used as a replacement.

Referring now to FIG. 16B, a cross-sectional view of mitral valve implant 900 is shown. FIG. 16B shows expandable member 902 having internal layer "i" and external layer "e". Expandable member 902 defines an internal chamber "c"

configured to receive an inflation medium. Internal layer "i" and external layer "e" may each be constructed out of a resiliently deformable material. For example, internal layer "i" may be constructed out of an open or closed cell foam material, which may be compressed into a catheter and delivered to the operative site. In some embodiments, internal layer "i" may be constructed out of shape memory alloy (e.g., copper-zinc-aluminum, copper-aluminum-nickel, nickel-titanium, etc.) forming a scaffold or strut matrix. Materials having shape memory properties may provide a layer that is capable of moving with expandable member 902 from an initial position to an expanded position and back. The resiliently deformable properties of expandable member 902 allow exterior layer "e" and interior layer "i" to at least partially conform with the shape of the leaflets of the heart valve. Interior layer "i" defines an opening or chamber within expandable member 902. This chamber "c" may be configured to receive an inflation medium from shaft 904. External layer "e" may be disposed over the internal layer "i" as shown in FIG. 16B. External layer "e" may be constructed out of a variety of different materials, including, but not limited to, expanded PolyTetraFluoroEthylene (EPTFE) and high silicone content, polyurethane copolymers such as Elasteon™ available from AorTech International PLC of the United Kingdom.

Figure 17A:
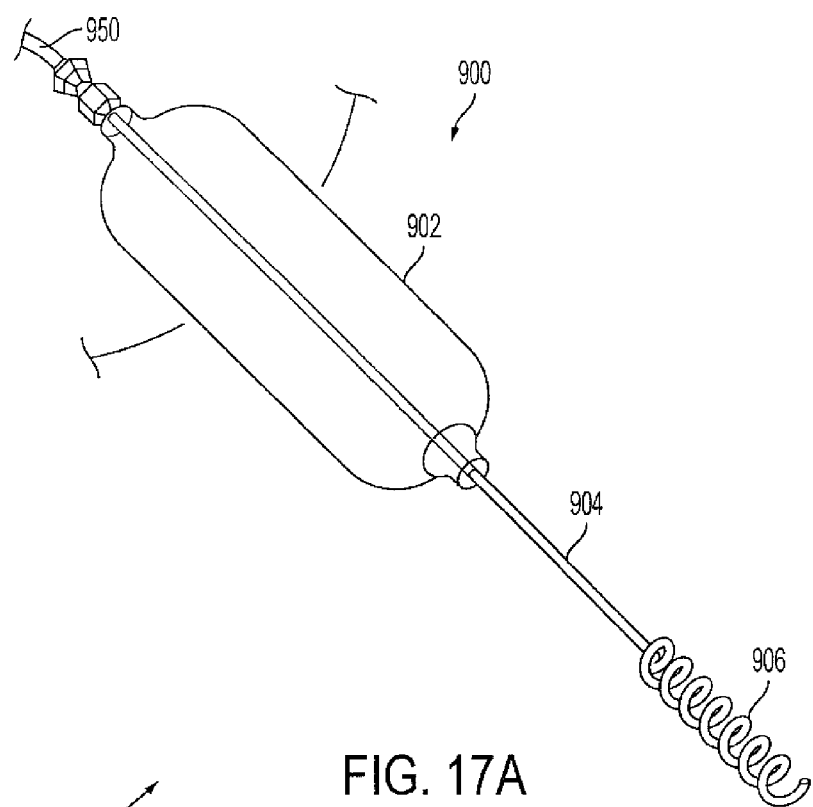
FIG. 17A depicts the mitral valve implant of FIGS. 16A-B shown in an at rest position.
Figure 17B:
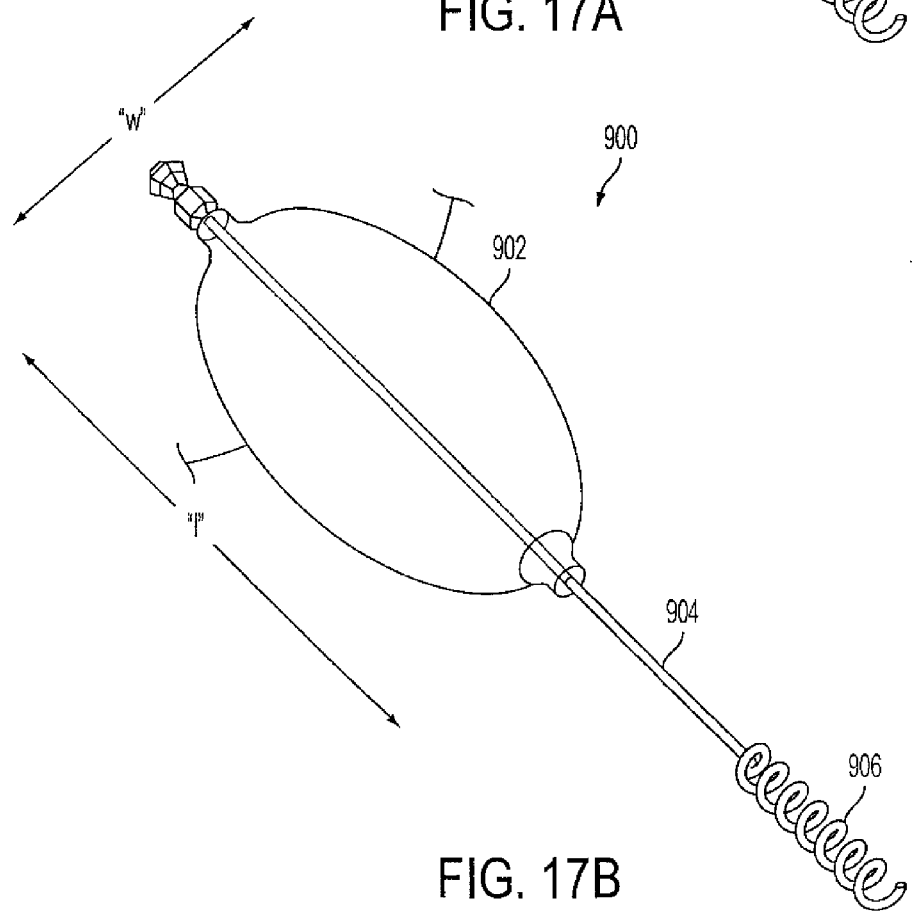
FIG. 17B depicts the mitral valve implant of FIGS. 16A-B shown in an expanded position.

Referring now to FIGS. 17a and 17b mitral valve implant 900 is shown in an initial and expanded position respectively. Implant 900 may be secured to an area of the heart using anchor portion 906. Expandable member 902 may be adjusted axially along shaft 904 until the desired position is reached (e.g., adjusting the depth of anchor portion 906, adjusting via shaft adjustment mechanisms, etc.). At this point an inflation medium may be fed into valve body 902 via a hose or other conduit 950. This medium may cause expandable member 902 to expand away from shaft 904 and possibly create contact with the leaflets of the mitral valve as shown in FIG. 17b.

In addition to the circular configuration shown in FIGS. 16-17, expandable member 902 may include a number of different shapes and configurations. Some possible geometries may include, but are not limited to, round, elliptical, pear shaped, self-shaping, hourglass shaped, etc. Expandable member 902 may include a uniform or irregular diameter along its length "l". For example, the width "w" of expandable member 902 may increase or decrease along its length "l" traveling between proximal end 905 and distal end 907.

Figures 18, 19:
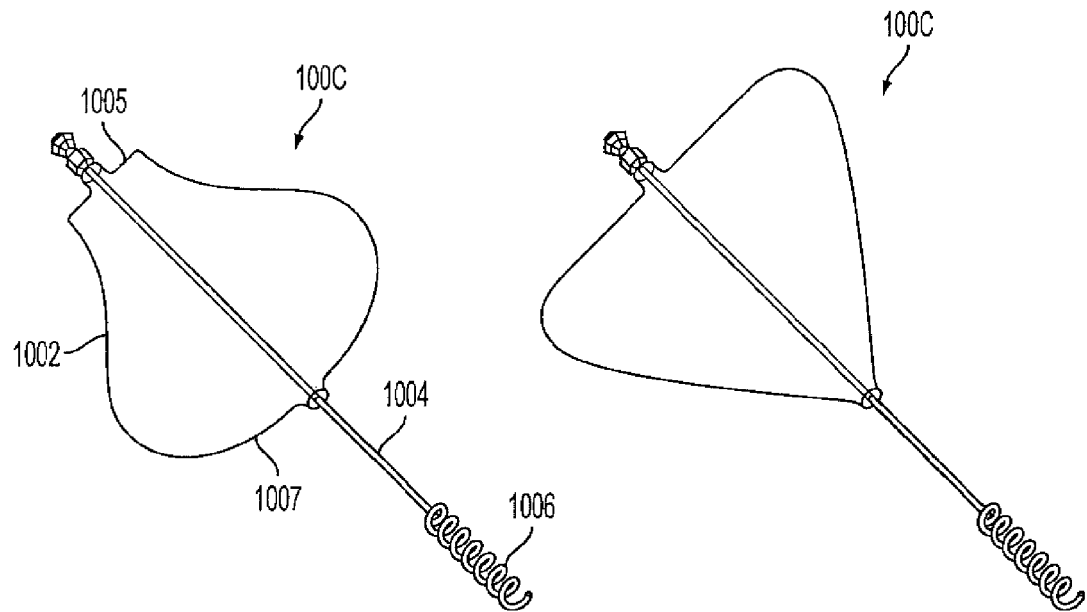
FIG. 18 is a perspective view of yet another embodiment of a mitral valve implant in accordance with the present disclosure.
FIG. 19 is a perspective view of another embodiment of a mitral valve implant in accordance with the present disclosure.

Referring now to FIG. 18, a mitral valve implant 1000 including a pear-shaped expandable member 1002 is shown. Implant 1000 may include shaft 1004, anchor portion 1006, and proximal and distal ends 1005, 1007 as described above. In this embodiment, expandable member 1002 is shown having a tapered configuration, increasing in diameter from a more narrow geometry to a wider geometry as the distal end 1007 of expandable member 1002 is approached. Of course, this tapered configuration could be altered and may include varying degrees of curvature. For example, the diameter of expandable member 1002 could decrease in diameter as the distal end 1007 of expandable member 1002 is approached.

Figures 20, 21:
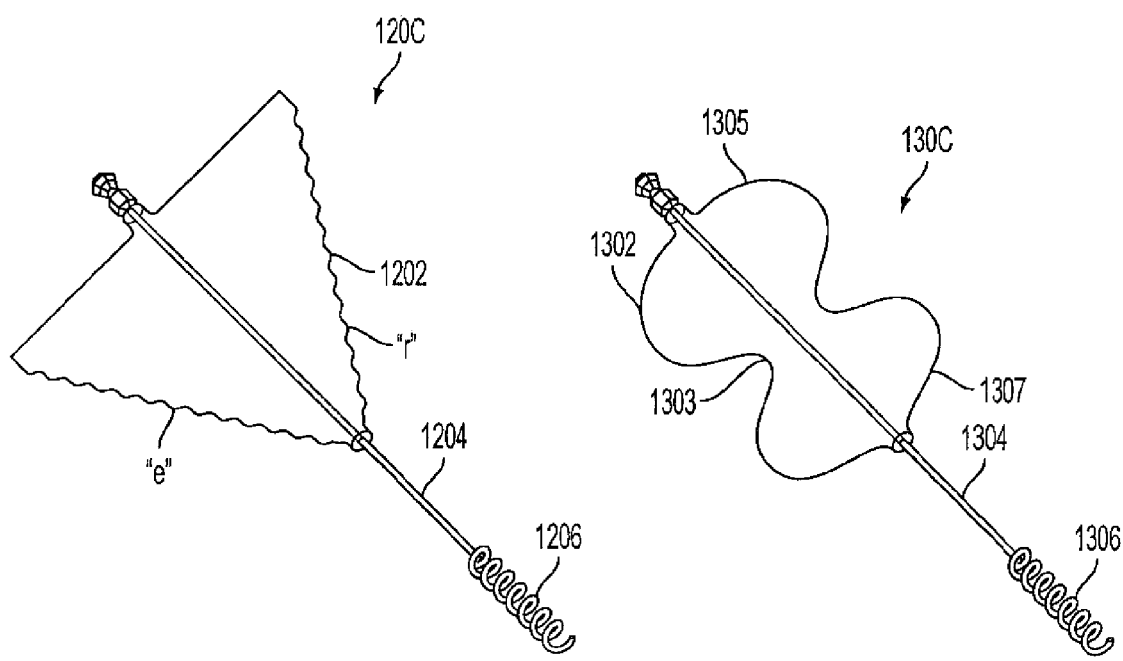
FIG. 20 is a perspective view of an embodiment of a mitral valve implant in accordance with the present disclosure.
FIG. 21 is a perspective view of yet another embodiment of a mitral valve implant in accordance with the present disclosure.

FIG. 19 shows another embodiment of a mitral valve implant 1100 having a heart-shaped or partially heart-shaped configuration. Implant 1100 may be positioned between the leaflets of the mitral valve and insufflated until the desired position is obtained. Of course, other shapes and configurations are also envisioned. For example, an additional embodiment of an implant 1200 is depicted in FIG. 20. Implant 1200 may include a plurality of ridges "r" or grooves capable of abutting with the mitral valve. The exterior surface of expandable member 1202 may include a variety of different surfaces and surface geometries. For example, ridges, grooves, and/or convex or concave indentations may be provided upon the exterior surface of expandable member 1202 to interact with the leaflets of the mitral valve. These variations upon the exterior surface may be used in accordance with any of the embodiments described herein.

FIG. 21 shows yet another embodiment of a mitral valve implant 1300. Mitral valve implant 1300 may include expandable member 1302, shaft 1304 and anchor portion 1306. Implant 1300 includes expanded proximal and distal ends 1305 and 1307 that connect via narrow central portion 1303. In some embodiments, implant 1300 may be positioned to allow for any portion of expandable member 1302 to contact the mitral valve. The expansion characteristics of central portion 1303, proximal end 1305 and distal end 1307 may be consistent or irregular. For example, in some embodiments, ends 1305 and 1307 may expand at substantially the same rate while central portion 1303 expands at a slower rate. This may be achieved using different construction methods for each section and/or constructing each section out of different materials or by using varying degrees of thickness. Of course, altering the design and/or material properties of the expandable member may be performed using any or all of the embodiments described herein.

Figure 22A:
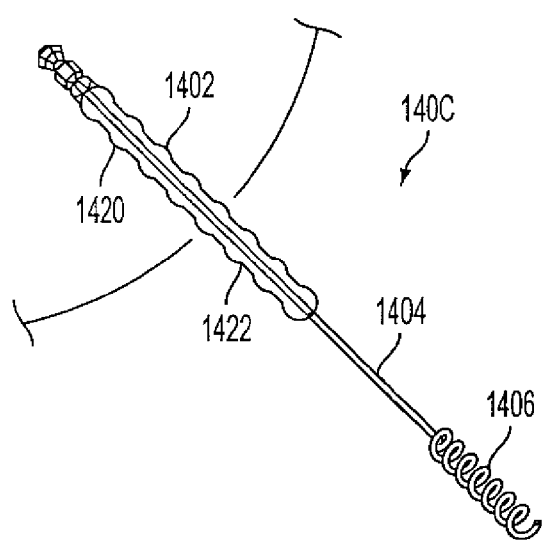
FIG. 22A is a perspective view of an additional embodiment of a mitral valve implant in accordance with the present disclosure.
Figure 22B:
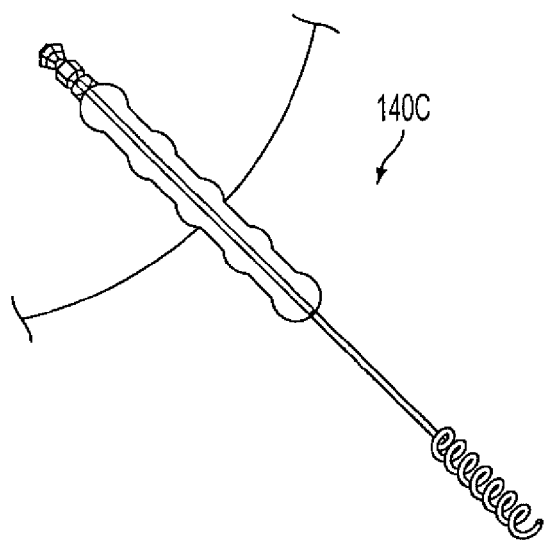
FIG. 22B depicts the mitral valve implant of FIG. 22A shown in an expanded position.

Referring now to FIGS. 22A and 22B, an additional embodiment of a mitral valve implant 1400 is shown. Mitral valve implant 1400 may include expandable member 1402, shaft 1404 and anchor portion 1406. FIG. 22A depicts implant 1400 in an "at rest" position. Implant 1400 may further include a plurality of protrusions 1420 connected via linkage portion 1422. Aspects of linkage portion 1422 and protrusions 1420 may be configured to receive an inflation medium and to expand in a transverse direction from shaft 1404. Protrusions 1420 may be expandable and may be further configured to receive gels or other substances, which may be capable of hardening after entering expandable member 1402. Some substances may maintain a self-shaping property, which may allow portions of expandable member 1402 to conform to the leaflets of the mitral valve. FIG. 22B shows an embodiment of implant 1400 in an expanded position. Implant 1400 may be expanded until protrusions 1420 and/or linkage portion 1422 contact the leaflets of the mitral valve.

Figure 23:
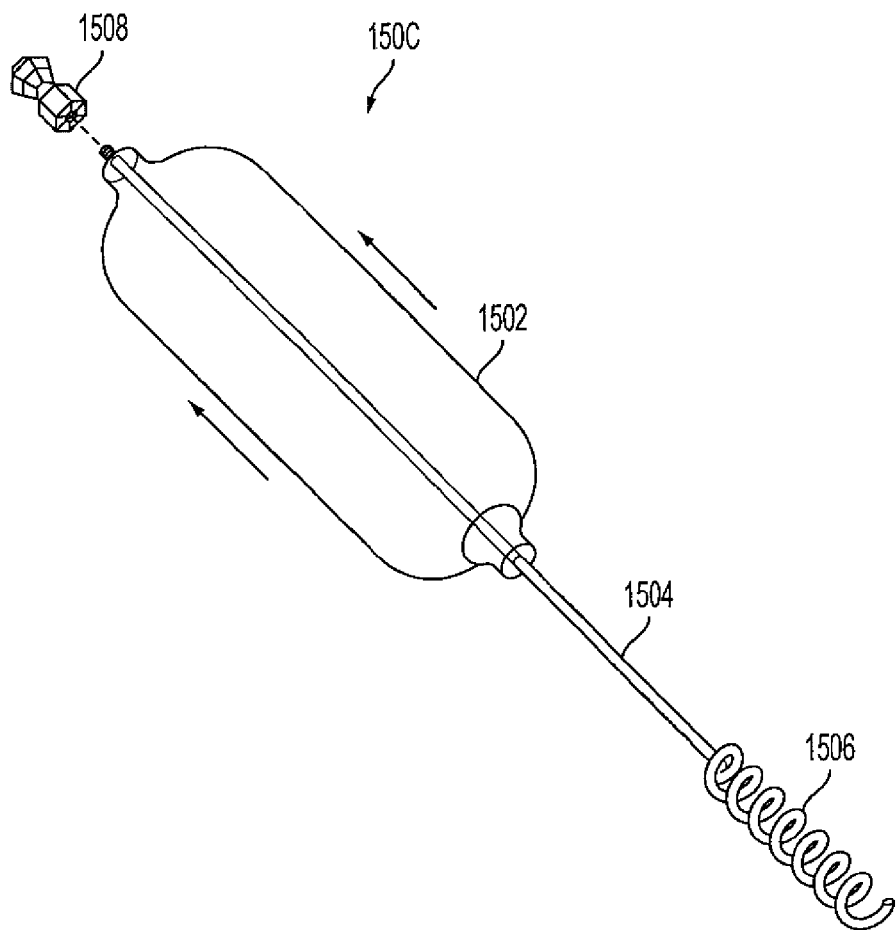
FIG. 23 is a perspective view of yet another embodiment of a mitral valve implant having a detachable valve body.

FIG. 23 provides an additional embodiment of mitral valve implant 1500 having a detachable expandable member 1502. Implant 1500 includes connector portion 1508, which may be a screw-fit, snap-fit or any other suitable configuration. In this embodiment, connector portion 1508 may be detached from expandable member 1502 and/or shaft 1504, allowing for the removal and/or replacement of expandable member 1502. In some embodiments, connector portion 1508 and expandable member 1502 may be permanently affixed. If so, the connector portion 1508 and expandable member 1502 may both need to be removed from shaft 1504. Shaft 1504 and anchor portion 1506 may remain in an anchored position while the existing expandable member is removed and replaced.

In some embodiments, the valve implant described herein may be used as a sizing mechanism in order to determine the approximate distance between the leaflets of the mitral valve. In other words, once the approximate size of the opening is determined via the valve implant a mold having a similar construction may be created and inserted in order to provide a more permanent device.

In some embodiments, the expandable member may be filled with a fluoro-visible material, which may provide the surgeon with improved visibility during the placement of implant. The implant may be positioned in an uninflated state and subsequently inflated after it has been placed in the appropriate position, possibly between the leaflets of the mitral valve. The fluoro-visible material may remain within the expandable member or may be removed and replaced with an alternative substance.

The implant herein has been disclosed above in the context of a mitral valve implant. An implant consistent with the present disclosure may also suitably be employed in other applications, e.g., as an implant associated with one of the other valves of the heart, etc. The present disclosure should not, therefore, be construed as being limited to use for reducing and/or preventing regurgitation of the mitral valve.

The terms valve body and expandable member, as described herein, may be used interchangeably to refer to a portion of the valve implant that may conform with at least a portion of at least one leaflet of a heart valve. While the depicted embodiments including expandable and/or recoverably deformable valve bodies have generally been shown configured as a expandable member consistent with a stationary valve implant, an expandable and/or recoverably deformable expandable member may be configured for use as part of a valve implant including a translating valve body. Similarly, while the valve implant embodiments including an expandable expandable member have been discussed in connection with transluminal and/or percutaneous delivery systems and/or procedures, such embodiments may also suitably be employed in connection with surgical delivery systems and/or methods. Additionally, other features and aspects of the various embodiments may also suitably be combined and/or modified consistent with the present disclosure. The disclosure herein should not, therefore, be limited to any particular disclosed embodiment, and should be given full scope of the appended claims.

What is claimed is:

1. A heart valve implant comprising:
  a shaft;
  an anchor coupled to one end of the shaft, the anchor configured to secure the heart valve implant to a patient's heart;
  an expandable member coupled to a part of the shaft, the expandable member comprising a resiliently deformable internal layer and a resiliently deformable external layer disposed over the internal layer, the resiliently deformable internal layer comprising a scaffold, wherein the expandable member defines a chamber configured to receive an inflation medium from an inflation device and to expand the expandable member from a compressed position to an expanded position; and
  a valve configured to seal said inflation medium within said chamber in the expanded position after disconnection from said inflation device such that the expandable member, when in the expanded position, is configured to at least partially restrict a flow of blood through the heart valve during systole upon contact with at least a portion of at least one leaflet of a heart valve.

2. The heart valve implant according to claim 1, wherein the resiliently external layer is constructed out of a high silicone content, polyurethane copolymer.

3. The heart valve implant according to claim 1, wherein the inflation medium is selected from the group comprising at least one of a gas, liquid, gel, and/or flouro-visible material.

4. The heart valve implant according to claim 1, wherein the expandable member is further configured to receive a hardening gel.

5. The heart valve implant according to claim 1, wherein the expandable member is controllably expandable to expand the member to a selectable cross-sectional diameter.

6. The heart valve implant according to claim 1, wherein the expandable member is expanded to a shape selected from the group consisting of round, pear-shaped, elliptical, hourglass-shaped, oval and heart-shaped.

7. The heart valve implant according to claim 1, wherein the expandable member is removably attached to the shaft.

8. The heart valve implant according to claim 1, wherein the expandable member is slidably coupled to the shaft.

9. The heart valve implant according to claim 1, wherein the expandable member is configured to determine the distance between a first leaflet and a second leaflet of a heart valve.

10. The heart valve implant according to claim 1, further comprising a connecting member removably coupled to the shaft.

11. The heart valve implant according to claim 1, wherein the shaft includes an adjustment mechanism configured to permit the axial movement of the expandable member along the shaft.

* * * * *

UNITED STATES PATENT AND TRADEMARK OFFICE
CERTIFICATE OF CORRECTION

PATENT NO. : 8,449,606 B2  
APPLICATION NO. : 11/748121  
DATED : May 28, 2013  
INVENTOR(S) : Eliasen et al.

Page 1 of 1

It is certified that error appears in the above-identified patent and that said Letters Patent is hereby corrected as shown below:

Title page 3, Item [56] (Other Publications), column 1, line 64, delete "health" and insert -- Heart --, therefor.

Title page 4, Item [56] (Other Publications), column 2, line 51, delete "Tempory" and insert -- Temporary --, therefor.

Title page 4, Item [56] (Other Publications), column 2, line 55, delete "Funcitonal" and insert -- Functional --, therefor.

Title page 7, Item [56] (Other Publications), column 1, line 61, delete "press122" and insert -- press/22 --, therefor.

Title page 8, Item [56] (Other Publications), column 1, line 29, delete "Indavertently" and insert -- Inadvertently --, therefor.

In the Claims

In column 20, line 18, in claim 3, delete "flouro" and insert -- fluoro --, therefor.

Signed and Sealed this  
Twenty-fourth Day of September, 2013

Teresa Stanek Rea  
*Deputy Director of the United States Patent and Trademark Office*